US012578330B2

(12) United States Patent
Sundrehagen et al.

(10) Patent No.: US 12,578,330 B2
(45) Date of Patent: Mar. 17, 2026

(54) METHODS FOR DETERMINING THE CONCENTRATION OF AN ANALYTE IN THE PLASMA FRACTION OF A SAMPLE OF WHOLE BLOOD

(71) Applicant: Gentian AS, Moss (NO)

(72) Inventors: Erling Sundrehagen, Moss (NO); Kathrin Sunde, Moss (NO); Camilla Fant, Kullavik (SE); Olov Wahlsten, Gothenburg (SE); Clara Mathilde Hidden, Vestby (NO)

(73) Assignee: Gentian AS, Moss (NO)

( * ) Notice: Subject to any disclaimer, the term of this patent is extended or adjusted under 35 U.S.C. 154(b) by 781 days.

(21) Appl. No.: 17/999,665

(22) PCT Filed: Jun. 18, 2021

(86) PCT No.: PCT/EP2021/066676
§ 371 (c)(1),
(2) Date: Nov. 22, 2022

(87) PCT Pub. No.: WO2021/255268
PCT Pub. Date: Dec. 23, 2021

(65) Prior Publication Data
US 2023/0204575 A1 Jun. 29, 2023

(30) Foreign Application Priority Data
Jun. 18, 2020 (SE) .................................... 2050735-6

(51) Int. Cl.
*A61B 5/1455* (2006.01)
*G01N 33/543* (2006.01)
(Continued)

(52) U.S. Cl.
CPC ....... *G01N 33/54388* (2021.08); *G01N 33/80* (2013.01); *G01N 2333/4727* (2013.01);
(Continued)

(58) Field of Classification Search
CPC ............. G01N 33/54388; G01N 33/80; G01N 2333/4727; G01N 2333/4737;
(Continued)

(56) References Cited

U.S. PATENT DOCUMENTS

2006/0281187 A1 12/2006 Emery et al.

FOREIGN PATENT DOCUMENTS

| JP | 6103776 B2 | 3/2017 |
| WO | 2009046227 A1 | 4/2009 |

(Continued)

OTHER PUBLICATIONS

Capiau, Sara, et al. "A novel, nondestructive, dried blood spot-based hematocrit prediction method using noncontact diffuse reflectance spectroscopy." Analytical Chemistry 88.12 (2016): 6538-6546. (Year: 2016).*

(Continued)

*Primary Examiner* — Bao-Thuy L Nguyen
*Assistant Examiner* — Christopher Evans
(74) *Attorney, Agent, or Firm* — Myers Bigel, P.A.

(57) ABSTRACT

The precision of a lateral flow assay for determining the concentration of an analyte in the plasma fraction of a sample of whole blood can be significantly improved by applying an integrated step for determining the hematocrit of the optionally diluted sample, and taking both hematocrit and dilution factor into account when calculating the concentration of the analyte. This is made possible inter alia by using a predetermined wavelength when taking an image of the sample after application to a substrate in the lateral flow assay device, and wherein said wavelength is selected based on the dilution factor used. This hematocrit measurement is advantageously integrated in lateral flow assay methods and devices for the measurement of an analyte in plasma and contributes significantly to an improved precision of such assays.

15 Claims, 12 Drawing Sheets

(51) Int. Cl.
    *G01N 33/80*        (2006.01)
    *G16H 10/40*        (2018.01)

(52) U.S. Cl.
    CPC ................ *G01N 2333/4737* (2013.01); *G01N 2333/585* (2013.01); *G01N 2333/8139* (2013.01)

(58) Field of Classification Search
    CPC ...... G01N 2333/585; G01N 2333/8139; B01L 2200/10; B01L 2300/0825; B01L 3/5023; A61B 5/1455
    See application file for complete search history.

(56)                      References Cited

FOREIGN PATENT DOCUMENTS

| WO | 2009108239 | A2 | 9/2009 |
|----|------------|-----|--------|
| WO | 2013147200 | A1 | 10/2013 |
| WO | 2015061598 | A1 | 4/2015 |

OTHER PUBLICATIONS

"International Preliminary Report on Patentability corresponding International Application No. PCT/EP2021/066676 mailed Sep. 28, 2022".
"International Search Report and Written Opinion corresponding International Application No. PCT/EP2021/066676 mailed Oct. 20, 2021".

* cited by examiner

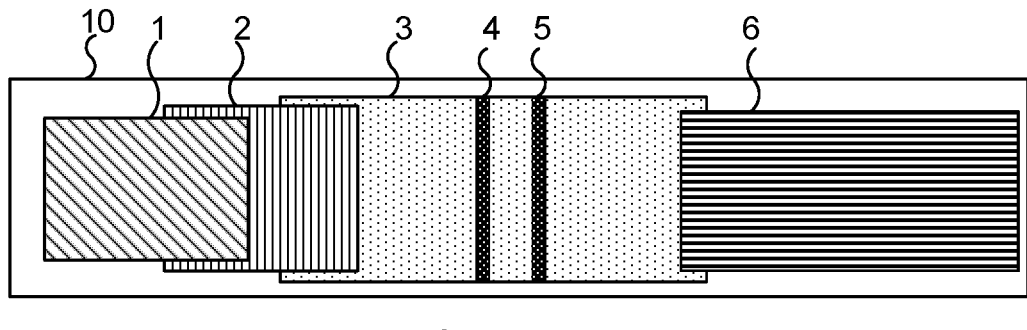
_Fig. 5_
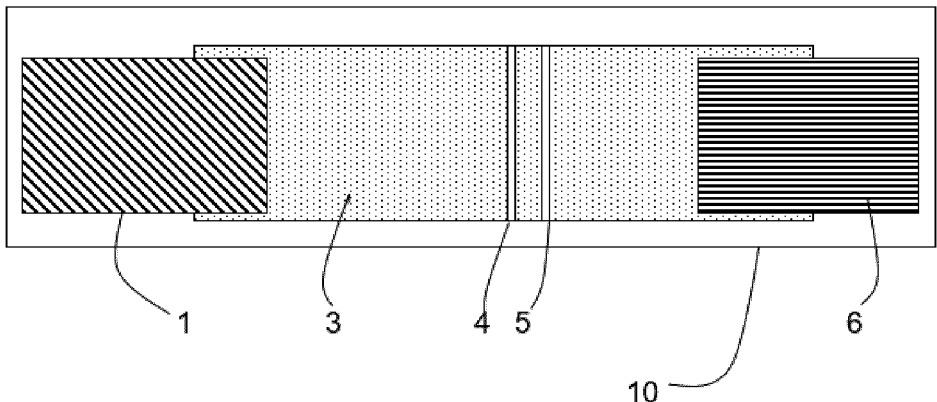
_Fig. 6_

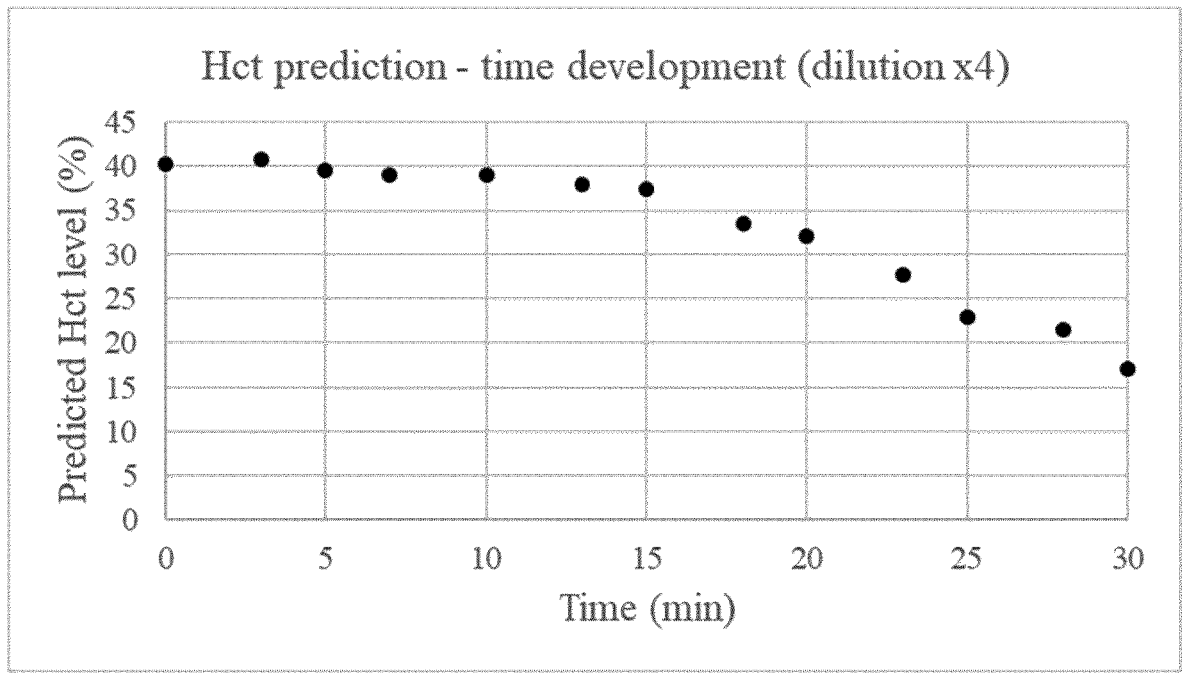
_Fig. 14_
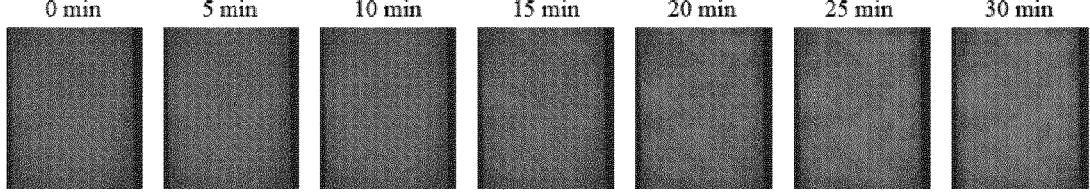
_Fig. 15_

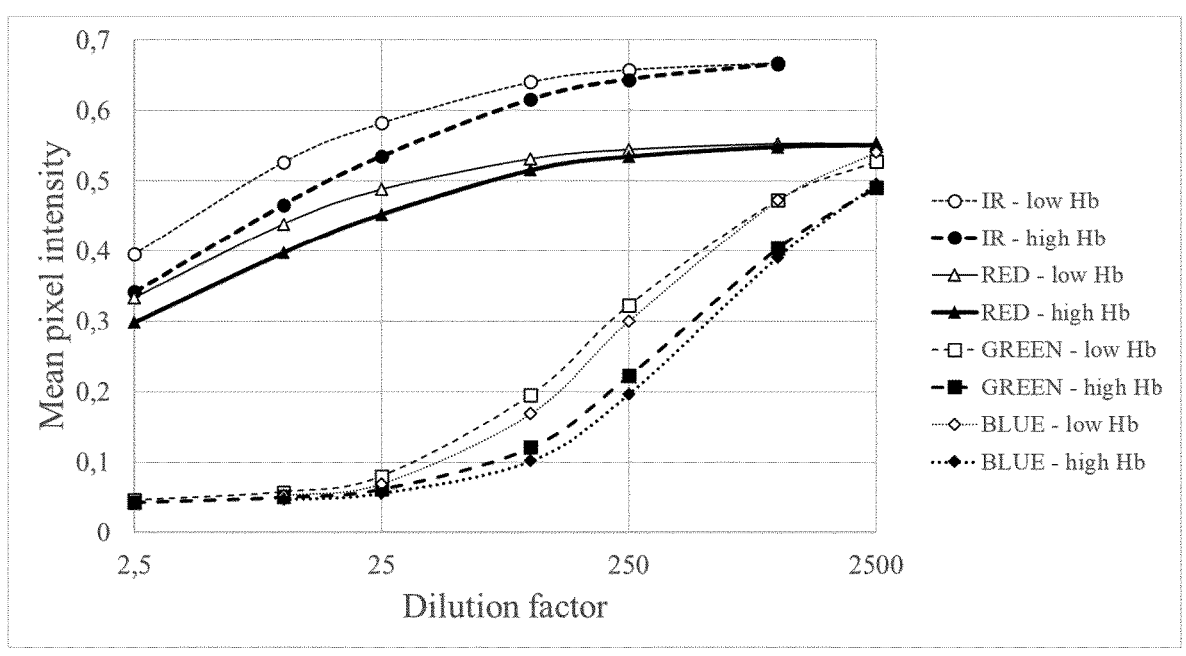
_Fig. 16_
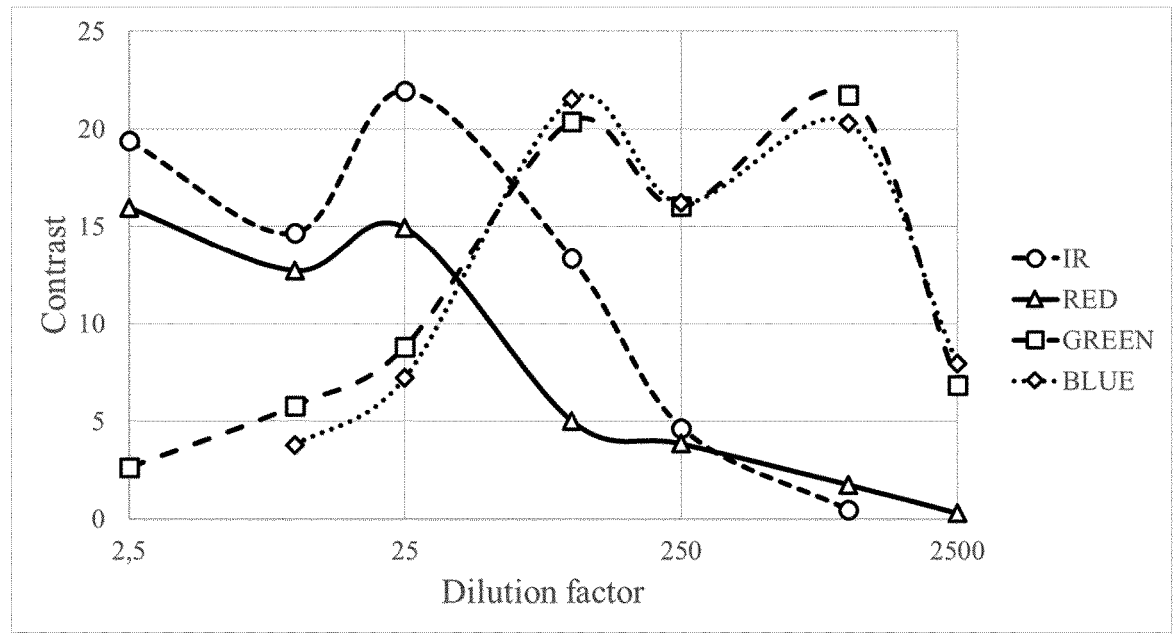
_Fig. 17_

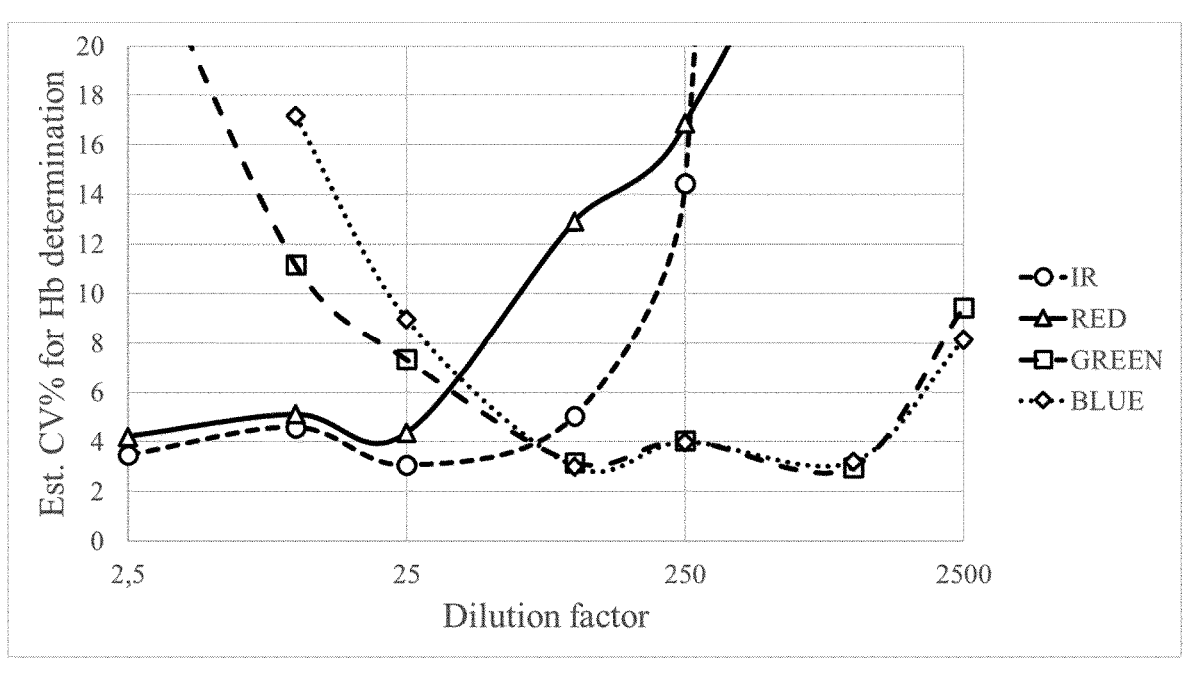
_Fig. 18_
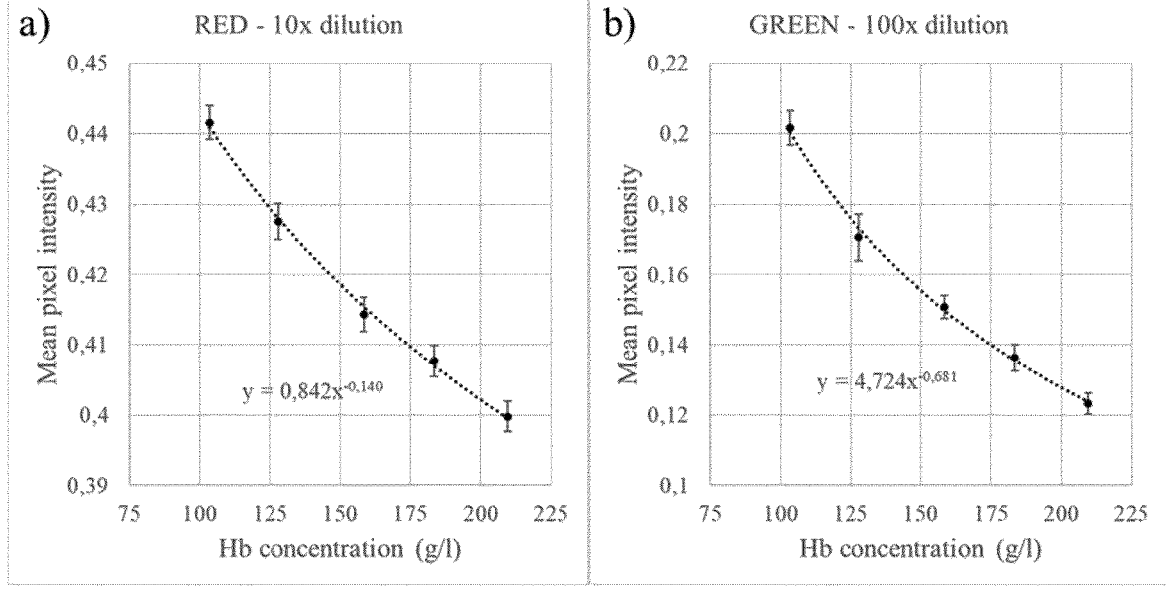
_Fig. 19_

METHODS FOR DETERMINING THE CONCENTRATION OF AN ANALYTE IN THE PLASMA FRACTION OF A SAMPLE OF WHOLE BLOOD

STATEMENT OF PRIORITY

This application is a 35 U.S.C. § 371 national phase application of PCT Application No. PCT/EP2021/066676 filed Jun. 18, 2021, which claims priority to Swedish Application No. 2050735-6 filed Jun. 18, 2020, the entire contents of each of which are incorporated by reference herein.

TECHNICAL FIELD

This disclosure relates to the field of clinical analysis, and in particular to methods and devices for handling samples of whole blood and determining a concentration of an analyte in the plasma fraction of said sample. The disclosure relates in particular to lateral flow assay methods and devices for handling samples of whole blood and quantitatively determining the hematocrit and a concentration of one or more analyte in the plasma fraction, while accounting for the hematocrit of said whole blood sample.

BACKGROUND

Blood tests are a cornerstone of modern medicine, and it is today possible to determine the presence and concentration of literally hundreds of analytes. Blood tests are used to determine the physiological and biochemical status of a patient, and the results are central in determining nutritional status, health, the presence or absence of various diseases, the effectiveness of a treatment, organ function and also for example to detect drug abuse. Methods and devices for this purpose range from comparatively simple test strips to automated clinical instruments, capable of holding reagents for performing hundreds of tests on a single sample.

Whole blood is comprised of erythrocytes, platelets and leukocytes suspended in plasma. In blood from healthy individuals, the erythrocytes constitute the clear majority of cells. The erythrocytes, also called red blood cells (RBC) contain hemoglobin (Hb), which gives blood its red colour and has oxygen-binding abilities. Plasma mainly consists of water (approx. 93%) but also of salts, various proteins and lipids as well as other constituents, e.g. glucose. The plasma also contains trace amounts of hundreds if not thousands of biochemical compounds out of which a great number are established clinical analytes, while others are still the subject of investigation. Tests or assays conducted in a laboratory setting are often based on plasma or serum. For Point-Of-Care (POC) applications, it is however preferable if a sample of whole blood can be used, avoiding the step of separating the serum or plasma prior to applying the sample to the assay.

Hemoglobin

Hemoglobin (Hb) is an iron-containing metalloprotein responsible for the transport of oxygen in the red blood cells of all vertebrates. In mammals, Hb makes up about 96 weight-% of the red blood cells' dry content and about 35 weight-% of the total content.

Methods for the measurement of Hb were first developed more than a century ago, making this one of the first diagnostic blood tests available to clinicians. Today, Hb concentration measurement is among the most commonly performed blood tests, usually as part of a complete blood count. For example, it is typically tested before or after blood donation. Results are reported in g/L, sometimes in g/dL or mol/L. Normal levels are 14 to 18 g/dl for men, 12 to 16 g/dl for women (11-14 g/dl for pregnant women), and 11-16 g/dl for children (Billet, 1990).

If the concentration is below normal, this is called anaemia. Anaemia can be due to blood loss, decreased red blood cell production, and increased red blood cell breakdown. In addition to blood donations, causes of blood loss include trauma and gastrointestinal bleeding, among others. Decreased production of red blood cells can be caused by iron deficiency, a lack of vitamin B12, thalassemia, and a number of neoplasms of the bone marrow. Increased breakdown of red blood cells can be due to a number of genetic conditions such as sickle cell anaemia, infections like malaria, and certain autoimmune diseases.

The hemiglobincyanide (HiCN) test originally developed in the 1950-ties remains the recommended method of the International Committee for Standardization in Haematology (ICSH) against which all new methods for the measurement of the concentration of Hb are judged and standardized. ICSH was founded in 1966 and has been active ever since, establishing and revising recommendations for the standardised HiCN method and organizing and supervising production and distribution of an international reference preparation, a sterile ampouled HiCN solution of exactly known concentration.

Portable hemoglobinometers such as the HemoCue® 201 device (HemoCue AB, Sweden) allow accurate determination of hemoglobin in a Point-of-Care setting, and at blood donation centres. The devices are essentially photometers which allow measurement of the colour intensity of solutions.

The measurements are made in disposable microcuvettes, which also act as reaction vessels. The reagents necessary for both the release of Hb from erythrocytes and for the conversion of Hb to a stable coloured product are present in dried form on the walls of the cuvette. All that is required is introduction of a small sample (typically 10 μL) of capillary, venous or arterial blood to the microcuvette and insertion of the microcuvette into the instrument. The instrument is factory pre-calibrated using the above mentioned HiCN standard, and the absorbance of the test solution is automatically converted to the concentration of total hemoglobin (ctHb). The result is displayed in less than a minute.

Reagent-less analysers have been on the market since 2006 (the HemoCue® 301) and recently, the DiaSpect™ (EKF Diagnostics plc/DiaSpect Medical GmbH) was introduced, using a reagentless cuvette, a photometric method, and providing results in approximately one second.

It is well known that quantitative colorimetric determination of Hb can be performed at 540 nm after first oxidizing hemoglobin and its derivatives (except sulfhemoglobin) to methemoglobin in the presence of an alkaline potassium ferricyanide and potassium cyanide solution (Drabkin's reagent). Methemoglobin reacts with potassium cyanide to form cyanomethemoglobin, which has a maximum absorption at 540 nm. The colour intensity measured at 540 nm is proportional to the total hemoglobin concentration.

A paper-based test for measuring Hb has also been disclosed in 2013 by Yang et al. (Yang et al., 2013). In this test, a 20 μL droplet of a mixture of blood and Drabkin's reagent is deposited onto patterned chromatography paper. The resulting blood stain is left to dry for 25 minutes, scanned and the digital images analysed based on a red/green/blue (RGB) colour model. The green channel showed the best linear fit and was selected to quantify Hb in the blood samples.

Hematocrit

The volume fraction of packed red blood cells in a blood sample is referred to as the hematocrit (Hct) and expressed as % of the total sample volume. Normal Hct levels are rather constant, in the range of 40% to 54% for adult males and 36% to 48% for adult women (Henny H. Billett, 1990, ibid). Deviations from these reference levels are generally regarded as the sign of a critical disease such as anaemia, leukaemia, a kidney infection, or a diet deficiency; but may also be an indication of an unambiguous condition, such as pregnancy, or even extensive exercise.

The interference of Hct is considered to be an important issue when measuring the concentration of different analytes in plasma or serum. Variations in Hct can cause serious errors in all qualitative and quantitative clinical blood analysis assays.

To illustrate the significance of knowing the Hct, one can consider two samples of whole blood, one obtained from a patient having low Hb, 100 g/l and a sample from a patient having very high Hb, 180 g/l, both values being physiologically relevant. The first patient will have a Hct of approximately 30% while the second patient has a Hct of approx. 54%. For a sample size of 25 µl, this means that for the first patient, there will be 17.5 µl plasma available for analysis, and for the second patient, only 11.5 µl. When determining the concentration of an analyte present in plasma, these variations may have considerable significance.

A method for Hct prediction using non-contact diffuse reflectance spectroscopy has been presented (Capiau, et al., 2016). The results indicated that mere scanning of a dried blood spot suffices to derive its approximate Hct. Venous blood was collected from consenting healthy volunteers in blood collection tubes with lithium heparin as anticoagulant. Dried blood spots were prepared at the day of blood collection by depositing 25 µL of blood onto Whatman 903 filter paper. The blood spots were always allowed to dry at ambient conditions for at least 2 h. The obtained dried blood spots were either analysed immediately after drying or stored in zip-locked plastic bags in the presence of a desiccant until analysis. The dried blood spots were found to be stable for at least 5 months at room temperature, and at least up to 3 days at elevated temperatures (60° C.). The dried blood spots were illuminated using a 10 W tungsten-halogen light source, and a spectrometer recorded the wavelength dependence of the reflected light intensity between 354 and 1042 nm.

An analysis technique using a histogram for the colorimetric quantification of blood hematocrit, was proposed in 2017, and the researchers developed a smartphone-based "histogram app" for the determination of hematocrit integrating the smartphone embedded camera with a microfluidic chip via a custom-made optical platform (Jalal et al., 2017).

U.S. Pat. No. 8,730,460 (Yan et al., Paper Based Spectrophotometric Detection of Blood Hemoglobin Concentration) discloses a paper-based spectrophotometric detection of blood Hb concentration, wherein spectrophotometric techniques are used to measure light transmission at specified wavelengths through a paper medium containing a blood sample. The light transmission information is then used in the calculation of blood Hb concentration. In certain embodiments, the paper medium may be chemically treated to lyse the blood sample prior to measurement of the light transmission information.

WO 2017/087834 (Cornell University, Erickson et al.) presents a general concept of a multiplex diagnostic assay cartridge for detection of a plurality of target molecules. One embodiment relates to a multiplex diagnostic assay cartridge having a pre-processing module and—distal to the sample addition well—parallel assay regions for a ferritin immunoassay, a C-reactive protein immunoassay region and a hemoglobin colorimetric assay region.

The prior art methods for determining Hct mainly rely on external or auxiliary equipment (e.g. centrifuges, hemoglobinometers etc.), reagents (e.g. potassium cyanide) and/or the denaturation of the blood sample (e.g. by mixing with reagents and/or drying the sample). It thus remains a challenge to enable a substantially simultaneous or directly sequential measurement of hematocrit and an analyte in the same sample, as simply and rapidly as possible, while maintaining a high accuracy or even improving the accuracy compared to available rapid tests for the analyte in question.

SUMMARY

The present inventors have found that the precision of the measurement of an analyte in a whole blood sample can be significantly improved by determining the hematocrit and taking this into account when calculating the concentration of the analyte, and more importantly, that this can be performed in a lateral flow assay setting without the use of auxiliary equipment, reagents and/or the denaturation of the blood sample.

Accordingly, a first aspect of the present disclosure relates to a lateral flow assay method for handling a sample of whole blood and determining a level of an analyte in a plasma fraction of said sample, comprising a step of determining a hematocrit value of said sample and applying said hematocrit value when determining the level of said analyte in said plasma fraction, wherein the method comprises the steps of i) diluting said sample with a substantially non-hemolysing buffer to a pre-determined dilution factor, producing a diluted sample, ii) applying said diluted sample to a substrate of a lateral flow assay device, iii) taking an image of said substrate within 1-600 seconds from when the applied sample has been absorbed in said substrate, iv) analysing said image to determine a value of at least one parameter from said image, v) correlating said value to values obtained for samples having known hematocrit values to obtain a value of hematocrit for said sample, vi) determining the level of said analyte down-stream in said lateral flow assay device, applying the dilution factor used in (i) and the hematocrit value of the sample obtained in (v) when determining the level of said analyte in the plasma.

In the above, the substrate is preferably illuminated at a pre-determined wavelength when taking the image in step iii), wherein said wavelength is selected based on the dilution factor used in step i).

Alternatively, the substrate is illuminated with white light and the image taken in step iii) is taken using an optical filter transmitting light of a pre-determined wavelength, wherein said transmitted wavelength is selected based on the dilution factor used in step i).

The sample is preferably diluted with an isotonic buffer to a dilution factor in the interval of 1-2500 depending on the analyte to be determined, the physiological concentration of said analyte, and the sensitivity of the assay. The sample volume can be chosen by a skilled person in the art, and can be, for example, 10 μl, 20 μl, 25 μl, 50 μl, 100 μl depending on architecture of the assay device in question.

According to one embodiment of the above first aspect, said image is taken while illuminating the substrate with applied sample with light having a wavelength in the interval of about 600 to about 950 nm when the dilution factor is 1 (no dilution) to 10.

According to another embodiment of the above first aspect, said image is taken while illuminating the substrate with applied sample with light having a wavelength in the interval of about 575 nm to about 950 nm when the dilution factor is above 10 but below 50.

According to another embodiment of the above first aspect, said image is taken while illuminating the substrate with applied sample with light having a wavelength in the interval of about 400 nm to about 575 nm when the dilution factor is 50 to 2500.

According to an alternative embodiment of the above first aspect, said image is taken while illuminating the substrate with applied sample with white light and using an optical filter transmitting light having a wavelength in the interval of about 600 nm to about 950 nm when the dilution factor is 1 (no dilution) to 10.

According to another alternative embodiment of the above first aspect, said image is taken while illuminating the substrate with applied sample with white light and using an optical filter transmitting light having a wavelength in the interval of about 575 nm to about 950 nm when the dilution factor is above 10 but below 50.

According to another alternative embodiment of the above first aspect, said image is taken while illuminating the substrate with applied sample with white light and using an optical filter transmitting light having a wavelength in the interval of about 400 nm to about 575 nm when the dilution factor is 50 to 2500.

According to an embodiment of the above first aspect and freely combinable with all embodiments thereof, reagents capable of conjugating to the analyte to be determined are provided in a flow path of said lateral flow assay device, for example in a conjugate section of the flow path of the lateral flow device, or in a separate conjugate pad, forming part of said flow path.

According to another embodiment of the above first aspect and freely combinable with all embodiments thereof, reagents capable of conjugating to the analyte to be determined are included in the dilution buffer.

According to an embodiment of the above first aspect and freely combinable with all embodiments thereof, said at least one parameter determined in iv) is the reflectance from the substrate with sample applied to it.

Preferably the reflectance is measured as the mean intensity of the pixels included in said image.

According to an embodiment of the above first aspect and freely combinable with all embodiments thereof, the image is taken within about 1 to about 600 seconds, preferably within about 1 to about 360 seconds, more preferably within about 1 to about 180 seconds, most preferably within about 1 to about 90 seconds from when the sample has been absorbed into said substrate.

Most preferably the image is taken within about 1 to about 30 seconds from when the sample has been absorbed into said substrate.

According to an embodiment of the above first aspect and freely combinable with all embodiments thereof, the substrate is a fibrous substrate capable of separating red blood cells and plasma.

Preferably said fibrous substrate is adapted to substantially avoid hemolysis of red blood cells in the sample.

According to an embodiment of the first aspect, the method includes a step of taking an image of the substrate before addition of the diluted sample.

Different buffers can be used for diluting the sample, one example of a substantially non-hemolysing buffer is a Tris-buffered isotonic saline solution, but other non-hemolysing buffers are known and/or can be prepared by a person skilled in the art.

The method according to the first aspect and any embodiments thereof can be applied to any clinically or scientifically relevant analyte which is detectable in plasma. By way of example, the analyte can be chosen from ferritin, transferrin, plasma calprotectin, C-reactive protein (CRP), cystatin C, plasma procalcitonin (PCT), NTproBNP, troponin T, troponin I, and anti-CCP antibodies.

A second aspect relates to a lateral flow assay device for handling a sample of whole blood and determining a concentration of an analyte in a plasma fraction of said sample, said device adapted for performing the method according to the first aspect and any embodiments thereof.

A lateral flow assay device according to the second aspect can be applied to the analysis of any clinically relevant analyte detectable in plasma. By way of example, the analyte can be chosen from ferritin, transferrin, plasma calprotectin, C-reactive protein (CRP), cystatin C, plasma procalcitonin (PCT), NTproBNP, troponin T, troponin I, and anti-CCP antibodies.

According to one embodiment of said second aspect, the analyte is ferritin and said device comprises a substrate configured to receive a sample of whole blood diluted with a buffer, a conjugate pad comprising anti-ferritin antibodies conjugated to a marker, a membrane with at least one test line of immobilized anti-ferritin antibodies, and an absorbent pad; and wherein said substrate, conjugate pad, membrane and absorbent pad form a lateral flow path.

Alternatively, the analyte is ferritin and said device comprises a substrate configured to receive a sample of whole blood diluted with a buffer comprising anti-ferritin antibodies conjugated to a marker, a membrane with at least one test line of immobilized anti-ferritin antibodies, and an absorbent pad; and wherein said substrate, membrane and absorbent pad form a lateral flow path.

According to another embodiment of said second aspect, the analyte is transferrin and said device comprises a substrate configured to receive a sample of whole blood diluted with a buffer, a conjugate pad comprising anti-transferrin antibodies conjugated to a marker, a membrane with at least one test line of immobilized anti-transferrin antibodies, and an absorbent pad; and wherein said substrate, conjugate pad, membrane and absorbent pad form a lateral flow path.

Alternatively, the analyte is transferrin and said device comprises a substrate configured to receive a sample of whole blood diluted with a buffer comprising anti-transferrin antibodies conjugated to a marker, a membrane with at least one test line of immobilized anti-transferrin antibodies, and an absorbent pad; and wherein said substrate, membrane and absorbent pad form a lateral flow path.

According to another embodiment of said second aspect, the analyte is plasma calprotectin and said device comprises a substrate configured to receive a sample of whole blood diluted with a buffer, a conjugate pad with anti-calprotectin antibodies conjugated to a marker, a membrane with at least one test line of immobilized anti-calprotectin antibodies, and an absorbent pad; and wherein said substrate, conjugate pad, membrane and absorbent pad form a lateral flow path.

Alternatively, the analyte is plasma calprotectin and said device comprises a substrate configured to receive a sample of whole blood diluted with a buffer comprising anti-calprotectin antibodies conjugated to a marker, a membrane with at least one test line of immobilized anti-calprotectin antibodies, and an absorbent pad; and wherein said substrate, membrane and absorbent pad form a lateral flow path.

According to another embodiment of said second aspect, the analyte is cystatin C and said device comprises a substrate configured to receive a sample of whole blood diluted with a buffer, a conjugate pad with anti-cystatin C antibodies conjugated to a marker, a membrane with at least one test line of immobilized anti-cystatin C antibodies, and an absorbent pad; and wherein said substrate, conjugate pad, membrane and absorbent pad form a lateral flow path.

Alternatively, the analyte is cystatin C and said device comprises a substrate configured to receive a sample of whole blood diluted with a buffer comprising anti-cystatin C antibodies conjugated to a marker, a membrane with at least one test line of immobilized anti-cystatin C antibodies, and an absorbent pad; and wherein said substrate, membrane and absorbent pad form a lateral flow path.

According to another embodiment of said second aspect, the analyte is plasma procalcitonin and said device comprises a substrate configured to receive a sample of whole blood diluted with a buffer, a conjugate pad with anti-procalcitonin antibodies conjugated to a marker, a membrane with at least one test line of immobilized anti-procalcitonin antibodies, and an absorbent pad; and wherein said substrate, conjugate pad, membrane and absorbent pad form a lateral flow path.

Alternatively, the analyte is plasma procalcitonin and said device comprises a substrate configured to receive a sample of whole blood diluted with a buffer comprising anti-procalcitonin antibodies conjugated to a marker, a membrane with at least one test line of immobilized anti-procalcitonin antibodies, and an absorbent pad; and wherein said substrate, membrane and absorbent pad form a lateral flow path.

According to another embodiment of said second aspect, the analyte is C-reactive protein (CRP) and said device comprises a substrate configured to receive a sample of whole blood diluted with a buffer, a conjugate pad with anti-CRP antibodies conjugated to a marker, a membrane with at least one test line of immobilized anti-CRP antibodies, and an absorbent pad; and wherein said substrate, conjugate pad, membrane and absorbent pad form a lateral flow path.

Alternatively, the analyte is C-reactive protein (CRP) and said device comprises a substrate configured to receive a sample of whole blood diluted with a buffer comprising anti-CRP antibodies conjugated to a marker, a membrane with at least one test line of immobilized anti-CRP antibodies, and an absorbent pad; and wherein said substrate, membrane and absorbent pad form a lateral flow path.

According to another embodiment of said second aspect, the analyte is an anti-CCP antibody and said device comprises a substrate configured to receive a sample of whole blood diluted with a buffer, a conjugate pad with a CCP peptide or peptides conjugated to a marker, a membrane with at least one test line of an immobilized CCP peptide or peptides, and an absorbent pad; and wherein said substrate, conjugate pad, membrane and absorbent pad form a lateral flow path.

Alternatively, the analyte is an anti-CCP antibody and said device comprises a substrate configured to receive a sample of whole blood diluted with a buffer comprising a CCP peptide or peptides conjugated to a marker, a membrane with at least one test line of an immobilized CCP peptide or peptides conjugated to a marker, and an absorbent pad; and wherein said substrate, membrane and absorbent pad form a lateral flow path.

According to another embodiment of said second aspect, the analyte is NTproBNP and said device comprises a substrate configured to receive a sample of whole blood optionally diluted with a buffer, a conjugate pad with anti NTproBNP antibodies conjugated to a marker, a membrane with at least one test line of immobilized NTproBNP antibodies, and an absorbent pad; and wherein said substrate, conjugate pad, membrane and absorbent pad form a lateral flow path.

Alternatively, the analyte is NTproBNP and said device comprises a substrate configured to receive a sample of whole blood diluted with a buffer comprising anti NTproBNP antibodies conjugated to a marker, a membrane with at least one test line of immobilized anti NTproBNP antibodies, and an absorbent pad; and wherein said substrate, membrane and absorbent pad form a lateral flow path.

According to another embodiment of said second aspect, the analyte is troponin T and said device comprises a substrate configured to receive a sample of whole blood diluted with a buffer, a conjugate pad with anti-troponin T antibodies conjugated to a marker, a membrane with at least one test line of immobilized troponin T antibodies, and an absorbent pad; and wherein said substrate, conjugate pad, membrane and absorbent pad form a lateral flow path.

Alternatively, the analyte is troponin T and said device comprises a substrate configured to receive a sample of whole blood diluted with a buffer comprising anti-troponin T antibodies conjugated to a marker, a membrane with at least one test line of immobilized anti-troponin T antibodies, and an absorbent pad; and wherein said substrate, membrane and absorbent pad form a lateral flow path.

According to another embodiment of said second aspect, the analyte is troponin I and said device comprises a substrate configured to receive a sample of whole blood diluted with a buffer, a conjugate pad with anti-troponin I antibodies conjugated to a marker, a membrane with at least one test line of immobilized troponin I antibodies, and an absorbent pad; and wherein said substrate, conjugate pad, membrane and absorbent pad form a lateral flow path.

Alternatively, the analyte is troponin I and said device comprises a substrate configured to receive a sample of whole blood diluted with a buffer comprising anti-troponin I antibodies conjugated to a marker, a membrane with at least one test line of immobilized anti-troponin I antibodies, and an absorbent pad; and wherein said substrate, membrane and absorbent pad form a lateral flow path.

A third aspect relates to a processor configured to execute a method according to the first aspect and any embodiments thereof.

A fourth aspect relates to a computer program product comprising software instructions stored in a memory, said software instructions adapted for prompting a device to execute a method according to the first aspect and any embodiments thereof.

The foregoing summary is illustrative only and is not intended to be in any way limiting. In addition to the illustrative aspects, embodiments and features described above, further aspects, embodiments and features will become apparent by reference to the following drawings and the detailed description.

BRIEF DESCRIPTION OF THE DRAWINGS

The invention is now described, by way of example, with reference to the accompanying drawings, in which:

FIG. 5 shows a schematic view from above of a device according to the embodiment illustrated in FIG. 3.

FIG. 6 shows a schematic view from above of a device according to the embodiment illustrated in FIG. 4, wherein a separate conjugate pad is excluded from the lateral flow assay. In such arrangement, a conjugate zone can be provided in a section of the sample pad (1).

FIG. 14 shows the deterioration of the quality of Hct prediction with time, based on images taken at different interval up to 30 min from the application of the sample, based on the results from Example 11.

FIG. 15 is a series of photographs taken at 0 min (directly at application of the sample) and with five-minute intervals up to 30 min from application of the sample. It can be seen how the appearance is practically constant in the first three photographs, but then starts to change. The results correspond to the trend visible in FIG. 14.

FIG. 16 is a graph showing the mean pixel intensity of diluted blood samples (low Hb and high Hb) dispensed onto a Fusion 5 filter. Images have been acquired with an ESEQuant Flex reader (Dialunox) illuminating with IR and different colour using LEDs (red, green, blue).

FIG. 17 is a graph where a qualitative measure, called "contrast" has been plotted against the dilution factor, describing how well the Hb concentration of a blood sample can be determined for IR and different illumination colour using different LEDs (IR, red, green, blue) within a wavelength interval of 400 nm-950 nm and across a range of dilution factors. A higher contrast value generally indicates a better precision of the Hb concentration determination.

FIG. 18 is a graph showing the estimated precision (CV %) in a Hb prediction model. The data used for FIGS. 16 and 17 were here converted to CV % based on the standard deviation for the measurements at low and high Hb and the assumption of a linear correlation between Hb and mean pixel intensity. The estimated precision for different dilution factors is show for different wavelengths (IR, red, green, and blue).

FIG. 19 shows two graphs a) and b), illustrating the mean pixel intensity of diluted blood samples for the two settings a) red LED illumination at 10× dilution, and b) green LED illumination at 100× dilution. Each Hb concentration is measured 5 times. The circular dots represent the mean and the error bars represent 1 std. To each data set a power function was fitted to be used as a model for predicting the Hb concentration directly from the mean pixel intensity.

DETAILED DESCRIPTION

Figure 1:
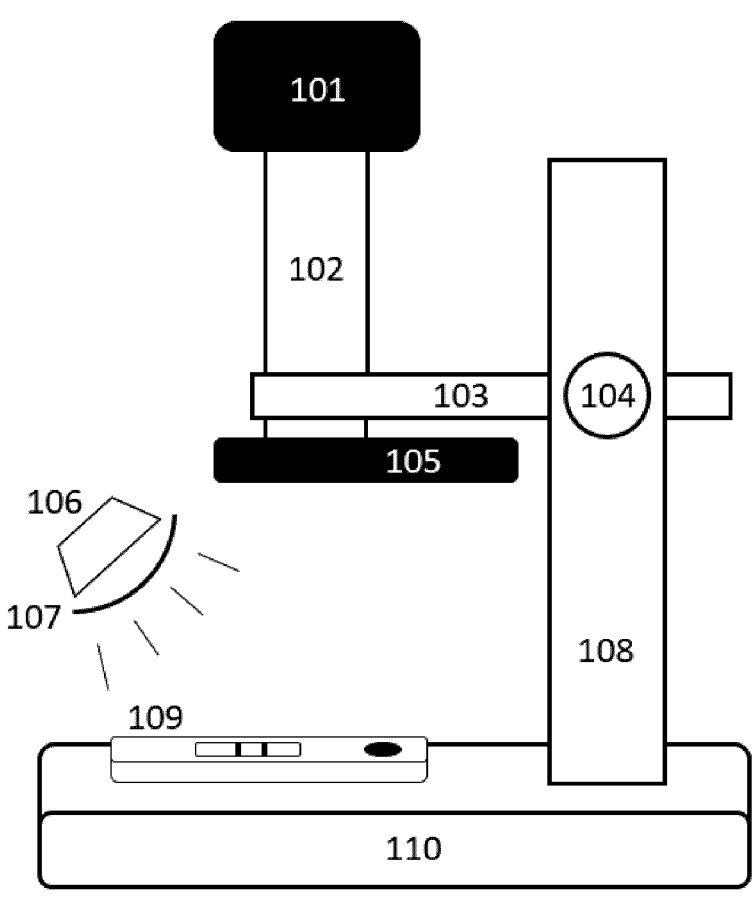
FIG. 1 shows a schematic of an imaging setup including a monochrome CMOS camera (101), focusing optics (102) and a filter wheel with a set of bandpass filters (105). The horizontal holder (103) attached to the vertical holder (108) and the height-adjustment knob (104) together allow for precise focusing to achieve sharp images. One or more white light sources (106) with diffusors (107) evenly illuminate a sample (109) placed on the sample holder (110). All images were acquired having the entire setup covered with a thick black cloth to block ambient light from disturbing the measurements. The sample (109) is only schematically indicated, here shown as a lateral flow assay test. In various experiments, different samples were used, ranging from pieces cut from filter material and other fibrous substrates, to partially or fully assembled lateral flow assay flow paths, with or without a plastic housing. The nature of the samples is disclosed in the individual examples.
Figure 2:
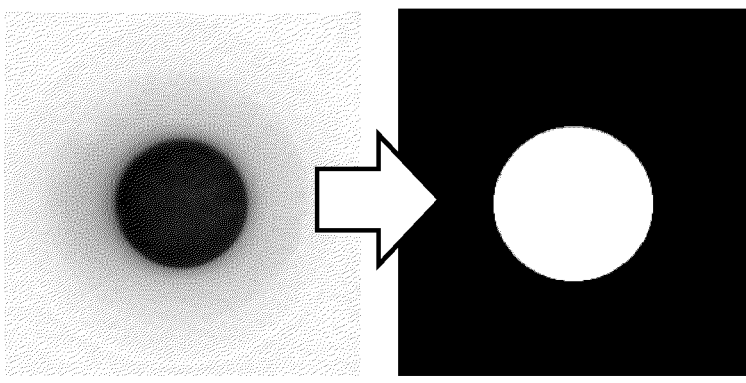
FIG. 2 illustrates how the relevant pixels can be identified starting from a photographic image of a diluted blood sample after it has been absorbed into the substrate. Based on the contrast between the sample and the background, the sample is masked, and the relevant pixels identified for further analysis.
Figure 3:
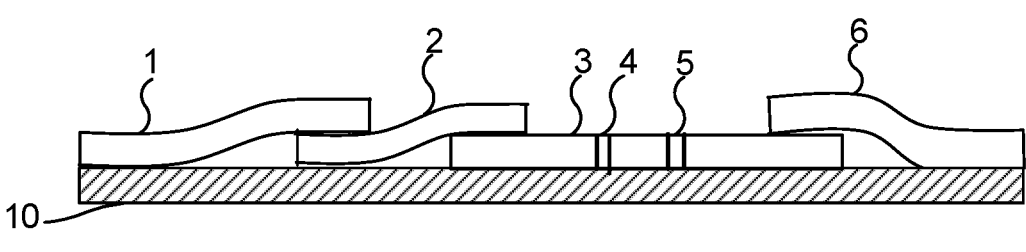
FIG. 3 shows a schematic cross-section of a lateral flow device according to an embodiment of the invention, comprising a portion for receiving a sample of whole blood, such as a sample pad (1) or a substrate, arranged in fluid connection with further substrates, media or filters (2, 3, 6) arranged on a support or backing (10). The media or filter shown as (2) can for example be a conjugate pad, comprising reagents or conjugates capable of specific binding to the analyte. A conjugate zone can however also be incorporated in the sample pad (1) The T (test) and C (control) lines are indicated as (4) and (5) respectively. It is conceived that multiple test and control lines can be provided, for example when determining more than one analyte in the sample, so called multiplex analysis, freely combinable with any of the embodiments disclosed herein.

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

The term "sample" as in "a sample of whole blood" refers to a sample that has been taken or extracted and physically removed from a human or animal body, and which sample will not be returned to said human or animal body.

The term "whole blood" as used herein, refers to blood with all its constituents. In other words, whole blood comprises both blood cells such as erythrocytes, leukocytes, and thrombocytes, and blood plasma in which the blood cells are suspended.

The term "plasma" or "plasma fraction", as used herein, denotes the blood's liquid medium and is an substantially aqueous solution containing water, blood plasma proteins, and trace amounts of other materials such as serum albumin, blood clotting factors, immunoglobulins (antibodies), hormones, carbon dioxide, various other proteins and various electrolytes (mainly sodium and chloride).

The term "blood serum" (or "serum"), as used herein, refers to plasma from which the clotting proteins have been removed.

The term "dilution factor" is defined as the ratio between final volume and initial volume of the solution, wherein the final volume is the volume of the solution after dilution, and the initial volume is the volume of original solution used for the dilution.

In further embodiments, the sample applied onto the substrate is a non-hemolysed sample of whole blood. The term "non-hemolysed", as used herein, indicates that after collecting the sample, the sample is handled in a fashion minimizing or preferably substantially preventing hemolysis, i.e. the disruption of red blood cells. Thus, the term non-hemolysed excludes disruptive sample processing such as drying the whole blood, e.g. on filter paper, for sample storage, and reconstitution of dried blood samples by re-dissolving in water, and the like. The term non-hemolysed however does not exclude that the sample of whole blood is cautiously diluted using an isotonic, non-hemolysing buffer.

Further, the storage of the samples per se, for example in a refrigerator or freezer, is not to be considered a processing step as defined above. Thus, the sample may be applied onto the substrate immediately after collection or it may be introduced into the device after storage of the sample for one or more hours to one or more days or weeks.

In addition, since whole blood samples comprise blood-clotting factors, which will cause the formation of blood clots upon prolonged storage of the samples and the presence of which may thus interfere with the subsequent analysis, the addition of anti-coagulants (i.e. inhibitors of blood clotting) is also not a treatment of the sample within the meaning of the present invention. Multiple compounds acting as anti-coagulants are well known in the art. Examples of anti-coagulants include inter alia natural or synthetic (i.e. obtained by chemical synthesis and/or recombinant DNA technology) vitamin K antagonists, natural or synthetic direct thrombin inhibitors, citrate, oxalate, heparin and ethylene-diamine-tetra acetic acid (EDTA).

In other embodiments, the whole blood sample is applied onto the substrate directly (i.e. in non-hemolysed form, as defined above) from a subject. Particularly, the whole blood sample may be obtained from a puncture at a fingertip of the subject. For example, after puncturing the fingertip, the leaking blood may be collected by contacting the blood with a capillary such that the blood is introduced by capillary force without external manipulation. The capillary may then be positioned relative to the assay device employed such that the blood can pass or can be actively transferred into the device. Alternatively, the punctured fingertip may be positioned immediately adjacent to one of the openings of the device, which are detailed below (e.g. by pressing the fingertip directly on such an opening) such that the blood leaking from the puncture may be introduced into the device. Preferably the capillary is emptied into a defined volume of an isotonic buffer, and thus the sample is diluted by a known, pre-defined dilution ratio or dilution factor. From this diluted sample, a pre-defined volume is collected and applied to the lateral flow device.

The dilution factor and the amount of sample added to the lateral flow device will vary depending on the assay that is performed on said lateral flow device. The dilution however serves the purpose of adding buffer to the sample and making the sample more accommodating for the analysis of the analyte or biomarker taking place down-stream in the lateral flow assay. At the same time, the fact that the sample is substantially non-hemolysed allows the application of the sample to an optically read assay, because discolouration due to hemolysis is largely avoided. As a result, the determination of Hct can be integrated into a lateral flow assay and the determination of Hct performed in line, in an up-stream section of the lateral flow assay strip while the analyte is determined down-stream in the same flow path of the lateral flow assay strip.

There are standardized methods for obtaining and handling a blood sample taken from a human or animal body, involving the use of needles, syringes, micro cuvettes etc.

These methods are well-known to persons skilled in the art. The currently most preferred type of sample is lithium heparin treated sample of whole blood. There are several blood collection tubes containing spray-coated lithium heparin readily available from various commercial supplies, e.g. the BD Vacutainer® available from BD, Oakville, Ontario, Canada.

The dilution of the sample is preferably automated, and there are currently available methods and devices for automatically extracting a defined volume of whole blood and introducing it into a defined volume of buffer, producing a diluted, non-hemolysed sample at a pre-defined dilution factor.

The term "substrate" refers to any substrate capable of receiving a sample of whole blood for analysis, preferably a flat substrate of homogenous colour, and most preferably a fibrous substrate, such as a cellulose-based or glass fiber-based filter capable of separating red blood cells and plasma and adapted to substantially avoid hemolysis of red blood cells in the sample.

The term "hematocrit value" or "hematocrit level" refers to the volume percentage (vol %) of red blood cells (RBC) in blood. The measurement depends on the number and size of red bloods cells, and varies with gender, age, and medical condition. It is normally about 40% to 54% for adult men and 36% to 48% for adult women. Because the purpose of red blood cells is to transfer oxygen from the lungs to body tissues, a blood sample's hematocrit level (Hct)—the red blood cell volume percentage—can become a point of reference of its capability of delivering oxygen. Hct levels that are too high or too low can indicate a blood disorder, dehydration, or other medical conditions. An abnormally low Hct may suggest anaemia, a decrease in the total amount of red blood cells, while an abnormally high Hct is called polycythemia.

Determining the Hct can be performed either directly, correlating Hct to a measured variable such as reflectance, or indirectly, correlating Hct to a variable such as Hb which in turn has been correlated to a measured variable such as reflectance.

The term "analyte" in this disclosure refers to any and all clinically relevant analytes present in blood and plasma, for example antibodies, hormones and proteins, for example but not limited to ferritin, plasma calprotectin, cystatin C, procalcitonin, NTproBNP, troponin T, troponin I and C-reactive protein. Examples of antibodies include autoantibodies as well as antibodies against infectious agents such as virus and bacteria, for example anti-CCP, anti-streptolysin-O, anti-HIV, anti-hepatitis (anti-HBc, anti-HBs etc), antibodies against *Borrelia*, and specific antibodies against microbial proteins.

A first aspect of the present disclosure relates to a lateral flow assay method for handling a sample of whole blood and determining a level of an analyte in a plasma fraction of said sample, comprising a step of determining a hematocrit value of said sample and applying said hematocrit value when determining the level of said analyte in said plasma fraction, wherein the method comprises the steps of i) diluting said sample with a substantially non-hemolysing buffer to a pre-determined dilution factor, producing a diluted sample, ii) applying said diluted sample to a substrate of a lateral flow assay device, iii) taking an image of said substrate within 1-600 seconds from when the applied sample has been absorbed in said substrate, iv) analysing said image to determine a value of at least one parameter from said image, v) correlating said value to values obtained for samples having known hematocrit values to obtain a value of hematocrit for said sample, vi) determining the level of said analyte down-stream in said lateral flow assay device, applying the dilution factor used in (i) and the hematocrit value of the sample obtained in (v) when determining the level of said analyte in the plasma.

In the above, the substrate is preferably illuminated at a pre-determined wavelength when taking the image in step iii), wherein said wavelength is selected based on the dilution factor used in step i).

Different light sources can be used, for example but not limited to light emitting diodes, LEDs. LEDs are available from many different commercial suppliers, and most commonly available colours are red, green, blue, yellow, amber and white. For the purpose of this application, the colours plus infrared (IR) are defined as follows:

400-475 nm—Blue
    475-550 nm—Green
    550-625 nm—Yellow
    625-700 nm—Red
    700-1000 nm—Infrared Alternatively, the substrate is illuminated with white light and the image taken in step iii) is taken using an optical filter transmitting light of a pre-determined wavelength, wherein said transmitted wavelength is selected based on the dilution factor used in step i). When a white light source is used, in combination with a suitable filter, transmitting light at a desired wavelength, including IR. There are commercial suppliers offering a full range of optical filters from ultraviolet (UV) to infrared (IR).

The sample is preferably diluted with an isotonic buffer to a dilution factor in the interval of 1-2500.

According to one embodiment of said aspect, the dilution is performed manually, for example by collecting capillary blood from drop of blood from a finger prick into a capillary having a pre-defined volume, and then emptying said capillary into a test tube containing a pre-defined volume of buffer and mixing, for example by shaking the tube. However, according to a preferred embodiment, the dilution is automated, meaning that it requires minimal manual operation and is performed in a highly repeatable fashion. Automatic sample preparation systems are commercially available, for example from Analytik Jena AG, Germany, Chemspeed technologies AG, Germany; and Becton, Dickinson & Co, USA. In an automated dilution operation, a pre-defined volume of sample is metered by a device and brought in contact with a pre-defined volume of buffer, either an isotonic buffer alone, or an isotonic buffer also comprising reagents, for example antibodies specific for the analyte to be detected. The automation can be very rudimentary, as exemplified by the Vacutainer® sample collection tube, or fully automated, as for example a fully automated sample preparation system, as supplied by any of the companies listed above.

According to an embodiment of said aspect, determining a hematocrit value in a) includes a step of taking an image of said substrate before addition of the diluted sample, producing a "blank" or "zero" measurement. This is preferably used to check the proper functioning of the camera and analysis routine, including the processor for executing the analysis, and the "blank" or "zero" measurement can also be used for accounting for the background of the substrate. The frequency of this "blank" or "zero" measurement is dependent on the stability of the method and the homogeneity of the substrate. For a stable method and/or homogenous substrate, it will be sufficient to perform the "zero" measurement on a daily or even only weekly basis, in order to calibrate the instrument. It may however be necessary to perform the zero measurement more frequently, in which case this can be done either by taking an image of each actual lateral flow assay test right before adding the sample to the test, or by using a designated calibration test, which is not used for patient samples.

According to another embodiment said buffer is an isotonic buffer adapted to maintaining the sample in substantially non-hemolysed form. A person skilled in the art is aware of how isotonic, non-hemolysing buffer solutions are prepared, and such solutions are also commercially available. One example is isotonic saline solution, but typically isotonic non-hemolysing buffers also comprise a pH stabilizer such as sodium phosphate or potassium phosphate. In addition, or alternatively, acetate, borate, carbonate, citrate or glutamate buffers can be used. Other additives that can be included in an isotonic buffer are for example bovine serum albumin, as well as detergents, such as Tween 20, and preservatives, such as sodium azide.

The dilution factor can be adapted to the clinically relevant concentration of the analyte in question. When the clinically/diagnostically relevant concentration of the analyte is comparatively high, a higher dilution factor may be used than if the clinically/diagnostically relevant concentration of the analyte is low. The dilution factor can also be adapted to the requirements of the lateral flow assay so that a sufficient volume of sample migrates through the conjugate pad, reacts with reagents and migrates across the T and C lines. Importantly, the present method and device allows such dilutions to be made without limiting the accuracy of the Hct determination.

According to another embodiment, also freely combinable with the previous embodiments, reagents capable of forming a conjugate with the analyte to be determined are included in the buffer. Examples of such reagents include but are not limited to antibodies with specific affinity for the analyte to be determined. Preferably said reagents, e.g. antibodies, are immobilized to a marker, such as colloidal gold nanoparticles, coloured latex nanoparticles, europium particles or the like. Most preferably the marker is chosen so that it does not interfere with the determination of Hct, i.e. a marker is chosen which has no or only minimal reflectance at the wavelength used in the measurement of Hb or Hct. The non-hemolysing buffer comprising reagents may also comprise other constituents, such as preservatives, stabilizers, optical enhancers and density adjusting agents, with the overruling requirement that the buffer does not cause hemolysis of the sample of whole blood.

Figure 4:
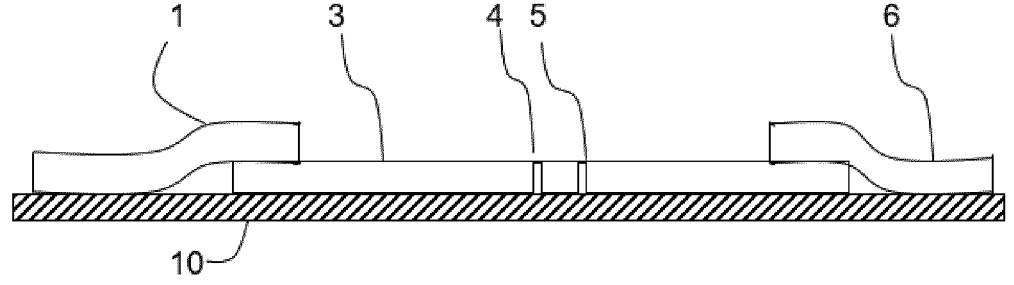
FIG. 4 shows a schematic cross-section of a device according to another embodiment of the invention, adapted for use in a method where the reagents or conjugates are included in the buffer or in the sample pad (1) close to the transition to the nitrocellulose filter (3), and the conjugates between for example an analyte and antibodies specific to this analyte, are formed in a mixture of sample and buffer, before the addition of a sample to the substrate (1). In this case, the lateral flow assay can comprise a filter (3) on which the T and C lines are arranged (4, 5) and an absorption pad (6), all preferably arranged on a backing (10). Also here, it is conceived that multiple test and control lines can be provided, for example when determining more than one analyte in the sample, so called multiplex analysis, freely combinable with any of the embodiments disclosed herein. It is also possible that a conjugate zone is provided in a section of the substrate (3), between the substrate (1) and the T and C lines (4, 5).

When the reagents are included in the buffer, or included in the sample pad, it is possible to omit a separate conjugate pad from the lateral flow assay device, as illustrated in FIGS. 4 and 6. This makes it possible to make the lateral flow assay device more simple and cheaper, and it also makes the reaction between analyte and reagents more efficient and is likely to improve the sensitivity and repeatability of the assay. Thus, according to an alternative embodiment, the conjugates can be arranged in a section of the sample pad without a separate conjugate pad, which also simplifies the production of the lateral flow assay.

Without wishing to be bound by theory, the present inventors contemplate that the reaction between analyte and reagents in the liquid buffer are more efficient and are completed faster than is the case in the conjugate pad of a lateral flow assay device. Based on this, the inventors postulate that no incubation is necessary, and that it will be sufficient to measure a predetermined volume of sample, add this to a volume of buffer, conforming to a pre-determined dilution factor, for example a dilution factor in the interval of 1-2500, shake or otherwise mix the sample, and then add a volume of sample to the substrate of the lateral flow assay. The Hct measurement is then performed substantially immediately, or at least within the first 600 seconds after the sample has been absorbed into the substrate. The concentration of the analyte can be read by measuring the signal from the T line at a point in time when the signal from the C line indicates that the sample has migrated through the filter/membrane.

According to one embodiment of the above first aspect, said image is taken while illuminating the substrate with applied sample with light having a wavelength in the interval of about 600 to about 950 nm when the dilution factor is 1 (no dilution) to 10.

According to another embodiment of the above first aspect, said image is taken while illuminating the substrate with applied sample with light having a wavelength in the interval of about 575 nm to about 950 nm when the dilution factor is above 10 but below 50.

According to another embodiment of the above first aspect, said image is taken while illuminating the substrate with applied sample with light having a wavelength in the interval of about 400 nm to about 575 nm when the dilution factor is 50 to 2500.

For example, as one embodiment of the above first aspect, said image is taken while illuminating the substrate with applied sample with light having a wavelength in the interval of about 535 nm to about 615 nm when the dilution factor is in the interval of 20 to 100.

According to an alternative embodiment of the above first aspect, said image is taken while illuminating the substrate with applied sample with white light and using an optical filter transmitting light having a wavelength in the interval of about 600 nm to about 950 nm when the dilution factor is 1 (no dilution) to 10.

According to another alternative embodiment of the above first aspect, said image is taken while illuminating the substrate with applied sample with white light and using an optical filter transmitting light having a wavelength in the interval of about 575 nm to about 950 nm when the dilution factor is above 10 but below 50.

According to another alternative embodiment of the above first aspect, said image is taken while illuminating the substrate with applied sample with white light and using an optical filter transmitting light having a wavelength in the interval of about 400 nm to about 575 nm when the dilution factor is 50 to 2500.

For example, as another alternative embodiment of the above first aspect, said image is taken while illuminating the substrate with applied sample with white light and using an optical filter transmitting light having a wavelength in the interval of about 535 nm to about 615 nm when the dilution factor is in the interval of 20 to 100.

According to an embodiment of the above first aspect and freely combinable with all embodiments thereof, reagents capable of conjugating to the analyte to be determined are provided in a flow path of said lateral flow assay device, for example in a conjugate section of the flow path of the lateral flow device, or in a separate conjugate pad, forming part of said flow path.

According to another embodiment of the above first aspect and freely combinable with all embodiments thereof, reagents capable of conjugating to the analyte to be determined are included in the dilution buffer.

According to an embodiment of the above first aspect and freely combinable with all embodiments thereof, said at least one parameter determined in iv) is the reflectance from the substrate with sample applied to it.

Preferably the reflectance is measured as the mean intensity of the pixels included in said image.

According to an embodiment of the above first aspect and freely combinable with all embodiments thereof, an image is taken within about 1 to about 600 seconds, preferably within about 1 to about 360 seconds, more preferably within about 1 to about 180 seconds, most preferably within about 1 to about 90 seconds from when the sample has been absorbed in said substrate.

The results shown in FIG. 14 show that the accuracy of the Hct measurement is substantially stable during the first 10 minutes (600 seconds) from application of the sample to the substrate, but that there is a rapid deterioration of the accuracy starting from 10-15 minutes from application. The photos shown in FIG. 15 also indicate that there is very little change in the appearance of the sample during the first 10 minutes.

Most preferably an image is taken within about 1 to about 30 seconds from when the sample has been absorbed in said substrate. Determining whether the sample has been absorbed in said substrate can be made manually, by observing if the volume of sample remains as a droplet on the surface of the substrate, or optically, for example based on reflectance. Before being absorbed, the liquid surface of the sample volume appears shiny and highly reflective, but when it has been absorbed, the surface texture of the substrate can be seen.

Preferably said fibrous substrate is adapted to substantially avoid hemolysis of red blood cells in the sample. The hemolysing properties of substrate can for example be influenced by adding heparin to the substrate, or by adjusting the hydrophilicity of the substrate. There are indications that making a polymer more hydrophilic reduces its hemolytic activity. Again, there are commercially available substrates, so called blood filters, capable of separating red blood cells from plasma without hemolysis.

According to another embodiment, also freely combinable with the previous embodiments, the method further comprises a calibration step by means of which a reference hematocrit level of a reference sample is determined by centrifugation.

In the alternative, the method further comprises a calibration step by means of which a reference hematocrit level is determined by first optically determining a concentration of hemoglobin in said sample using an independent standardized method such as a commercial hemoglobinometer or the HiCN test, and then converting said hemoglobin concentration to a hematocrit level.

The method is applicable to any analyte detectable in the plasma fraction, such as but not limited to ferritin, transferrin, plasma calprotectin, C-reactive protein (CRP), cystatin C, plasma procalcitonin (PCT), NTproBNP, troponin T, troponin I, and anti-CCP antibodies.

Another aspect of the present disclosure relates to a lateral flow assay device for handling a sample of whole blood and determining a concentration of an analyte in a plasma fraction of said sample, said device adapted for performing the method according to the first aspect and any one of the embodiments thereof.

The methods disclosed herein are applicable to any clinically relevant analyte which can be detected in plasma, such as but not limited to an analyte chosen from ferritin, transferrin, plasma calprotectin, C-reactive protein (CRP), cystatin C, plasma procalcitonin (PCT), NTproBNP, troponin T, troponin I, and anti-CCP antibodies.

According to a specific embodiment, the analyte is ferritin and said device comprises a substrate configured to receive a sample of whole blood diluted with a buffer, a conjugate pad with anti-ferritin antibodies conjugated to a marker, a membrane with at least one test line of immobilized anti-ferritin antibodies, and an absorbent pad, said substrate, conjugate pad, membrane and absorbent pad forming a lateral flow path.

In the alternative, the buffer comprises the anti-ferritin antibodies conjugated to a marker, and the conjugate pad is omitted from the lateral flow assay strip.

According to a specific embodiment, the analyte is transferrin and said device comprises a substrate configured to receive a sample of whole blood diluted with a buffer, a conjugate pad with anti-transferrin antibodies conjugated to a marker, a membrane with at least one test line of immobilized anti-transferrin antibodies, and an absorbent pad, said substrate, conjugate pad, membrane and absorbent pad forming a lateral flow path.

In the alternative, the buffer comprises anti-transferrin antibodies conjugated to a marker, and the conjugate pad is omitted from the lateral flow assay.

According to a specific embodiment, the analyte is plasma calprotectin and said device comprises a substrate configured to receive a sample of whole blood diluted with a buffer, a conjugate pad with anti-calprotectin antibodies conjugated to a marker, a membrane with at least one test line of immobilized anti-calprotectin antibodies, and an absorbent pad, said substrate, conjugate pad, membrane and absorbent pad forming a lateral flow path.

In the alternative, the buffer comprises anti-calprotectin antibodies conjugated to a marker, and the conjugate pad is omitted from the lateral flow assay.

According to another specific embodiment, the analyte is cystatin C and said device comprises a substrate configured to receive a sample of whole blood diluted with a buffer, a conjugate pad with anti-cystatin C antibodies conjugated to a marker, a membrane with at least one test line of immobilized anti-cystatin C antibodies, and an absorbent pad, said substrate, conjugate pad, membrane and absorbent pad forming a lateral flow path.

In the alternative, the buffer comprises the anti-cystatin C antibodies conjugated to a marker, and the conjugate pad is omitted from the lateral flow assay strip.

According to a specific embodiment of a lateral flow assay, the analyte is plasma procalcitonin and said device comprises a substrate configured to receive a sample of whole blood diluted with a buffer, a conjugate pad with anti-procalcitonin antibodies conjugated to a marker, a membrane with at least one test line of immobilized anti-procalcitonin antibodies, and an absorbent pad, said substrate, conjugate pad, membrane and absorbent pad forming a lateral flow path.

In the alternative, the buffer comprises the anti-procalcitonin antibodies conjugated to a marker, and the conjugate pad is omitted from the lateral flow assay strip.

Another embodiment is a lateral flow assay, wherein the analyte is C-reactive protein (CRP) and said device comprises a substrate configured to receive a sample of whole blood diluted with a buffer, a conjugate pad with anti-CRP antibodies conjugated to a marker, a membrane with at least one test line of immobilized anti-CRP antibodies, and an absorbent pad, said substrate, conjugate pad, membrane and absorbent pad forming a lateral flow path.

In the alternative, the buffer comprises the anti-CRP antibodies conjugated to a marker, and the conjugate pad is omitted from the lateral flow assay strip.

Yet another embodiment is a lateral flow assay device, wherein the analyte is an anti-CCP antibody and said device comprises a substrate configured to receive a sample of whole blood diluted with a buffer, a conjugate pad with a CCP peptide or peptides conjugated to a marker, a membrane with at least one test line of an immobilized CCP peptide or peptides conjugated to a marker, a membrane with at least one test line of immobilized antibodies, and an absorbent pad, said substrate, conjugate pad, membrane and absorbent pad forming a lateral flow path.

In the alternative, the buffer comprises the CCP peptide or peptides conjugated to a marker, and the conjugate pad is omitted from the lateral flow assay strip.

Another embodiment is a lateral flow assay device according to the second aspect, wherein the analyte is NTproBNP and said device comprises a substrate configured to receive a sample of whole blood diluted with a buffer, a conjugate pad with anti-NTproBNP antibodies conjugated to a marker, a membrane with at least one test line of immobilized anti-NTproBNP antibodies, and an absorbent pad, said substrate, conjugate pad, membrane and absorbent pad forming a lateral flow path.

In the alternative, the buffer comprises anti-NTproBNP antibodies conjugated to a marker, and the conjugate pad is omitted from the lateral flow assay.

Another embodiment is a lateral flow assay device according to the second aspect, wherein the analyte is troponin T and said device comprises a substrate configured to receive a sample of whole blood diluted with a buffer, a conjugate pad with anti-troponin T antibodies conjugated to a marker, a membrane with at least one test line of immobilized anti-troponin T antibodies, and an absorbent pad, said substrate, conjugate pad, membrane and absorbent pad forming a lateral flow path.

In the alternative, the buffer comprises anti-troponin T antibodies conjugated to a marker, and the conjugate pad is omitted from the lateral flow assay.

Another embodiment is a lateral flow assay device according to the second aspect, wherein the analyte is troponin I and said device comprises a substrate configured to receive a sample of whole blood diluted with a buffer, a conjugate pad with anti-troponin I antibodies conjugated to a marker, a membrane with at least one test line of immobilized anti-troponin I antibodies, and an absorbent pad, said substrate, conjugate pad, membrane and absorbent pad forming a lateral flow path.

In the alternative, the buffer comprises anti-troponin I antibodies conjugated to a marker, and the conjugate pad is omitted from the lateral flow assay.

Other aspects relate to a processor configured for converting reflectance values into a hematocrit level based on stored values of reflectance obtained for known hematocrit levels. Further, said processor is configured for taking the hematocrit level of a sample into account when calculating the value of another analyte present in plasma, in a setting where a sample of whole blood has been subjected to analysis. Said processor is provided using any combination of one or more of a suitable central processing unit (CPU), multiprocessor, microcontroller, digital signal processor (DSP), application specific integrated circuit etc., capable of executing software instructions stored in a memory, which can thus be a computer program product. The processor can be configured to execute any one of the methods disclosed herein, for example the methods defined in the claims attached hereto.

This memory can be any combination of random-access memory (RAM) and read only memory (ROM). The memory also comprises persistent storage, which, for example, can be any single one or combination of magnetic memory, optical memory, solid-state memory or even remotely mounted memory.

A data memory is also provided for reading and/or storing data during execution of software instructions in the processor. This data memory can be any combination of random-access memory (RAM) and read only memory (ROM).

A device and/or a system for lateral flow assay as disclosed herein can further comprise an I/O interface for communicating with other external entities. Optionally, the I/O interface also includes a user interface.

Other components of such devices are omitted in order not to obscure the concepts presented herein.

It is surprising that the above-mentioned analytes, present in plasma, can be accurately measured in a whole blood sample applied to a lateral flow test, and that a correction for variations in Hct can be performed regardless of dilution factor. The methods and devices disclosed herein offer many benefits in the field of diagnostics, in particular in the Point-of-Care setting.

One important advantage of the methods disclosed herein is that they do not rely on the use of any reagents for the determination of Hct and/or Hb. This not only simplifies the analysis, it also reduces the cost, as well as the risk, considering that the most frequently used reagents in Hb measurements are potassium ferricyanide and potassium cyanide, two highly toxic chemicals.

The elimination of reagents such as potassium ferricyanide and potassium cyanide has an additional advantage in that the lateral flow assay device becomes more stable during storage and can be approved for longer shelf-life as these and other reagents are prone to absorb moisture and/or react with other components of the assay.

Another advantage is the rapid response time, making it possible to have a result already during a visit to a physician or clinic, when screening blood donors etc. The rapid response time also makes it possible to integrate the determination of Hb and Hct into assays determining the concentration of other analytes in plasma, and to correct for variations in Hct. The present inventors have shown that this significantly improves the precision of the measurement of an analyte present in the plasma fraction of a whole blood sample, compared to measurements where an average Hct (average for the total population or average for the gender of the patient) is used. An integrated measurement of Hct is significantly more reliable than methods where the Hct is estimated based on the patient's gender, age and possibly health status. An integrated measurement of Hct is also more reliable than a separate analysis using an external device, followed by manual correction of the measured value of the analyte.

Yet another advantage is that the immediate measurement, in contrast to prior art methods that require lengthy drying of the samples, helps to avoid mix-ups of samples, avoids long waiting time for the patient, or when the method is automatized, allows higher through-put.

In addition to being fast and simple, the method disclosed herein is surprisingly accurate. Based on the experience obtained by the inventors so far, the accuracy is approximately ±7 g/l Hb or about ±2% Hct.

Another advantage is that camera sensor technology, or alternatively any other detector arrangement suitable for the stated purpose, is relatively cheap and easily available, making it economical to build analysis devices utilizing the inventive concept. The method is also well suited for automation, which is another important advantage. The camera sensor can be adapted to read a parameter used for quantifying the Hct and the same or a different parameter for quantifying the concentration of the analyte (the T line) and also the control (the C line).

As specified in the particular embodiments of the first aspect, an image can either be taken while illuminating the sample with light (or IR) having a pre-determined wavelength, or illuminated with white light, combined with the use of an optical filter transmitting light of a desired wavelength. This alternative approach offers considerable flexibility in the construction of a reader for handing the lateral flow test.

A particular advantage is that with the possibility of diluting the whole blood sample, the determination of Hct can become an integrated part of any lateral flow assay, and the requirement for multiple steps or partitioning of the sample and separate handling or separate assays is avoided.

The methods disclosed herein can also be integrated in or performed simultaneously or sequentially with existing and future clinical analysis methods, as a separate step in the sample preparation, as an initial step in the handling of the sample in the assay device, for example, when a sample is applied to a so-called blood filter for the separation of red blood cells from plasma. It is in this context a significant advantage that the wavelength interval (range), in particular the interval 400 nm to 950 nm, is equally applicable to all fibrous substrates capable of separating red blood cells from plasma. It is also an advantage that the determination of Hct is performed without hemolysing the blood, as this allows the integration of the method into assays where hemolysis is undesired, either because the discolouration of the plasma would interfere with the reading of the result, or where hemolysis releases substances which interfere with the analyte or reagents, compromising the assay.

Further, the capability to handle samples of whole blood eliminates the need for preparatory steps, such as the separation or extraction of plasma, and makes the method and assay well-suited for point-of-care use. The present method and device also make it possible to dilute the sample depending on the physiologically and clinically relevant concentration or reference concentration of each analyte, which make it possible to fine-tune each assay for the specific analyte, while maintaining a high accuracy based on the capability to account for individual variations in Hct.

EXAMPLES

Example 1. Ferritin Quantification Assay Based on Lateral Flow

Materials and Methods

Figure 7:
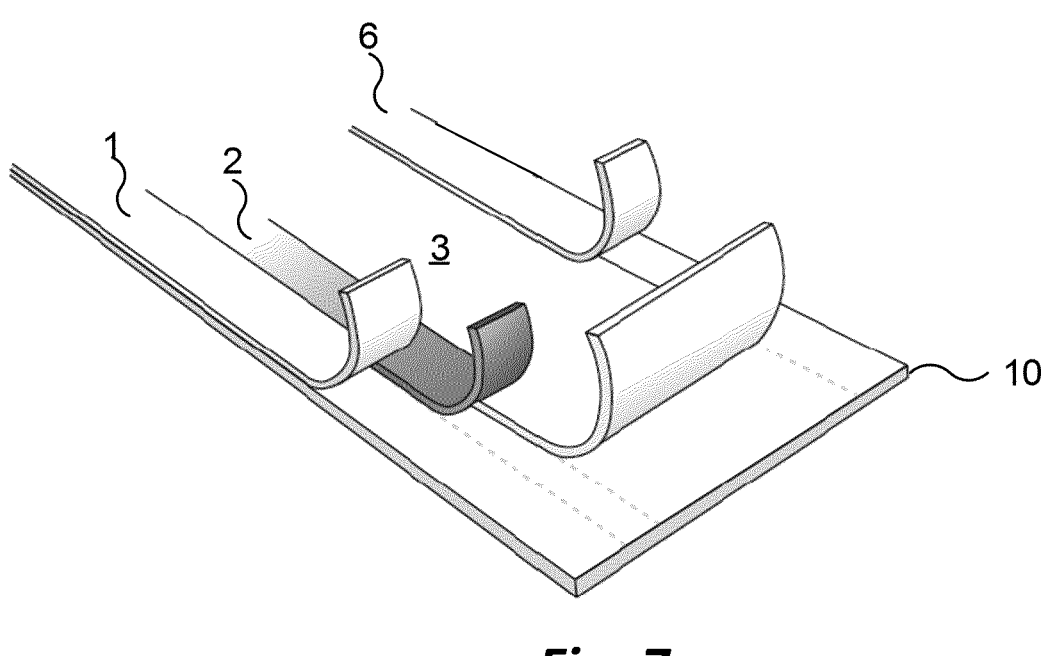
FIG. 7 illustrates an intermediate product used in the assembly of a lateral flow test, having a support or backing (10), and media or filters (1), (2), (3) and (6) arranged on said support. When this intermediate product is cut crosswise, lateral flow assay strips are formed, where (1) corresponds to the substrate or sample addition pad, (2) is the conjugate pad, (3) is the filter where the test line (4) and control line (5) can be arranged, and (6) is the absorbent pad or wicking pad, all arranged on a support or backing (10).
Figure 8:
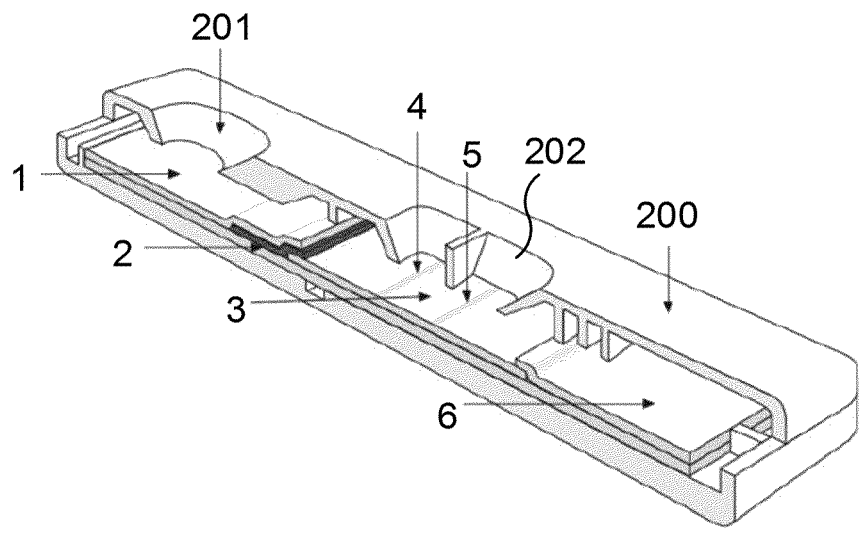
FIG. 8 is a cross section of a prototype assay device, showing a housing (200), enclosing inter alia the filters or support (1), (2), (3) and (6), and having a sample port (201) and one or more openings (202) exposing the test line and control line, (4) and (5) respectively. It is also here conceived that multiple test and control lines can be provided, for example for determining more than one analyte in the sample, so called multiplex analysis, freely combinable with any of the embodiments disclosed herein.

The general construction of the lateral flow assay used in the examples is shown in FIGS. 7 and 8.

Ferritin standards (60, 120, 180, 240, 300, 360, 420, 480, 540 and 600 ng/ml, and 1, 10, 100 and 1000 ng/ml) were prepared by diluting human liver ferritin (Code: P103-7, BBI Solutions) in a buffer consisting of 10 mM Tris-HCl, 140 mM NaCl, 1 ml/L ProClin 950, 1% BSA, pH 7.4.

Anti-ferritin antibodies (IgG) were obtained from BBI Solutions (Ferritin pAb Code: BP230-3) and Europium conjugated with anti-ferritin antibodies were prepared using the Europium conjugation kit from Expedeon Ltd., UK, according to the manufacturer's protocol. A solution of ~2.3×10E10 Europium particles/ml (0.01%) was used, and stored in a buffer containing 2 mM borate, 10% trehalose, 1 ml/L ProClin 950, at pH 9.5. A conjugate pad (2) was prepared by soaking a glass fiber pad (GFCP203000, Millipore/Merck KGaA, Germany) in this solution and subsequently dried overnight in an oven at 37° C.

In a second example, the conjugate pad was prepared with anti-human-ferritin-conjugated colloidal gold. Gold nanoparticles (InnovaCoat® GOLD—20 OD 80 nm gold conjugation kit, Expedeon Ltd., UK), was conjugated to anti-ferritin antibodies (BBI Solutions, Code no. BP230-3) according to the manufacturer's protocol. The conjugated nanoparticles were diluted to 1.1×10E10 particles/ml (OD=1) using a buffer consisting of 2 mM borate, 10% trehalose, 1 ml/L ProClin 950, at pH 9.5. A conjugate pad (2) was prepared by soaking a glass fiber pad (GFCP203000, Millipore/Merck KGaA, Germany) in this solution and subsequently dried overnight in an oven at 37° C.

In a third example, the conjugate pad was prepared with anti-human-ferritin-conjugated coloured latex beads. Black latex beads (Latex conjugation kit—400 nm Black, Expedeon Ltd., UK), was conjugated to anti-ferritin antibodies (BBI Solutions, Code no. BP230-3) according to the manufacturer's protocol. The conjugated latex beads were diluted to ~2.8×10E9 particles/ml (0.01%) using a buffer consisting of 2 mM borate, 10% trehalose, 1 ml/L ProClin 950, at pH 9.5. A conjugate pad (2) was prepared by soaking a glass fiber pad (GFCP203000, Millipore/Merck KGaA, Germany) in this solution and subsequently dried overnight in an oven at 37° C.

A lateral flow test strip was constructed by attaching a sample pad (1) chosen from two different glass fiber filters (LF1 and MF1, both from GE Healthcare), a conjugate pad (2), and an absorbent pad (6) onto a membrane backing card (10) with a pre-attached membrane (3) chosen from two different nitrocellulose membranes (Hi-Flow Plus 90, HF090MC100, and Hi-Flow Plus 180, HF180MC100, both from Millipore/Merck KGaA, Germany) where 90 and 180 indicate the wicking rates, i.e. it takes the liquid 90 or 180 seconds to travel 4 cm across the membrane. The different components were assembled with approx. 2 mm overlap to ensure good wicking.

A test line (4) and control line (5) were printed on the membrane (3) using an EASY PRINTER™ from MDI Membrane Technologies Ltd., India, using a solution of 1 mg/ml anti-ferritin (IgG) for the test line (4) and 1 mg/ml anti-IgG (goat anti-rabbit IgG, sigma Aldrich code no. SAB3700883-2 mg) for the control line (5). The membrane and backing card were dried overnight in an oven at 37° C., sprayed with a blocking solution (SuperBlock™ T20 (TBS) Blocking Buffer, code no. 37536, Thermo Fisher Scientific), and dried at 37° C. for an additional 2 hours. This produced an intermediate product as shown in FIG. 7.

Thin strips, approx. 4 mm wide and approx. 60 mm long, were cut using a paper cutter. These strips were placed in a plastic housing as shown in FIG. 8. The plastic housing (200) had a sample port (201) exposing part of the sample pad (1) and a window (202) exposing the test line (4) and control line (5).

1.1 Liver Ferritin Standards

10 µl of each standard were prediluted to a final volume in an assay buffer of 100 mM Tris-HCl, 50 mM NaCl, 1.5% Tween, 1% BSA, pH 7.4 using an automatic pipette. 75 µl of the prediluted standards were added to the sample pad.

For detection using anti-human-ferritin-conjugated Europium beads, the membrane was illuminated with a UV LED producing light at approximately 365 nm, and the emission was measured at approximately 610 nm using a CCD sensor equipped with a dichroic filter. A reading was taken after 5 minutes. The results indicate a good sensitivity at the relevant concentration interval, 100 ng/ml.

For detection using anti-human-ferritin-conjugated gold nanoparticles, the membrane was illuminated with a LED producing light at approximately 525 nm, and reflected light was captured with a CCD sensor. A reading was taken after 5 minutes. Preliminary results indicate a good sensitivity at the relevant concentration interval, 100 ng/ml.

For detection using anti-human-ferritin-conjugated coloured latex beads, the membrane was illuminated with a LED producing light at approximately 525 nm, and reflected light was captured with a CCD sensor. A reading was taken after 5 minutes. Preliminary results indicate a good sensitivity at the relevant concentration interval, 100 ng/ml.

The test line intensity showed an almost linear correlation to the concentrations. Additionally, it can be noted that the control line stayed practically constant, indicating that aggregation of detection particles is not likely to be pronounced.

1.2 Blood Samples—Ferritin Detection Only

Whole blood samples were obtained from healthy volunteers and tested using the lateral flow assay disclosed herein. The blood sample (10 μl) was prediluted in 90 μl assay buffer (70 mM Tris-HCl, 80 mM NaCl, 1% tween 20, 1% BSA, 0.01% proClin 950, pH 7.4) and transferred to the sample pad (MF1, GE healthcare) using an automatic pipette. After 5 minutes the intensity of test line and control line was evaluated using a CCD camera.

For detection using anti-human-ferritin-conjugated Europium beads, the membrane was illuminated with a UV LED producing light at approximately 365 nm, and the emission was measured at approximately 610 nm using a CCD sensor equipped with a dichroic filter. The plasma ferritin concentration in this sample was evaluated using Randox ferritin immunoassay (https://www.randox.com/ferritin/) on Architect c4000, a clinical chemistry analyser (Abbot Core Laboratory, Abbot Park, Illinois, USA).

For detection using anti-human-ferritin-conjugated gold nanoparticles, the membrane was illuminated with a LED producing light at approximately 525 nm, and the reflected light was captured with a CCD sensor. The plasma ferritin concentration in this sample was evaluated to using Randox ferritin immunoassay (https://www.randox.com/ferritin/) on Architect c4000.

For detection using anti-human-ferritin-conjugated coloured latex beads, the membrane was illuminated with a LED producing light at approximately 525 nm, and the reflection was measured using a CCD sensor. The plasma ferritin concentration in this sample was evaluated using Randox ferritin immunoassay (https://www.randox.com/ferritin/) on Architect c4000.

1.3 Blood Samples with Detection of Both Hb and Ferritin on the Same Test Strip

Whole blood samples were obtained from healthy volunteers and tested using the lateral flow assay disclosed herein. The blood sample (10 μl) was prediluted in 90 μl assay buffer (70 mM Tris-HCl, 80 mM NaCl, 1% tween 20, 1% BSA, 0.01% proClin 950, pH 7.4) and transferred to the sample pad (MF1)) using an automatic pipette.

Immediately after sample application, the Hb-level was read i in the sample application window. The paper was illuminated with warm LED spotlights (2800-3000 K) and the reflection was measured using a CMOS sensor (as schematically shown in FIG. 1).

5 minutes after Hb-reading, the intensity of the ferritin test line and control line was evaluated using a CCD camera. Hb of this sample was determined using average of manual Randox Drabkin's and HemoCue 201.

For detection using anti-human-ferritin-conjugated Europium beads, the membrane was illuminated with a UV LED producing light at approximately 365 nm, and the emission was measured at approximately 610 nm using a CCD sensor equipped with a dichroic filter. The plasma ferritin concentration in this sample was evaluated using Randox ferritin immunoassay (https://www.randox.com/ferritin/) on Architect c4000.

For detection using anti-human-ferritin-conjugated gold nanoparticles, the membrane was illuminated with warm LED spotlights (2800-3000 K) and the reflection was measured using a CMOS sensor. The plasma ferritin concentration in this sample was evaluated using Randox ferritin immunoassay (https://www.randox.com/ferritin/) on Architect c4000.

For detection using anti-human-ferritin-conjugated coloured latex beads, the membrane was illuminated with a LED producing light at approximately 525 nm, and the reflection was measured using a CCD sensor. The plasma ferritin concentration in this sample was evaluated using Randox ferritin immunoassay (https://www.randox.com/ferritin/) on Architect c4000.

Example 2. Influence of Hct on Ferritin Measurements

A lateral flow assay comprising a glass fiber-based sample pad, and in fluid connection therewith, a conjugate pad with anti-ferritin antibodies, and downstream on a filter medium, immobilized anti-ferritin antibodies or fragments is assembled and tested. Upon application of a prediluted whole blood sample on the sample pad, the reflectance of the blood sample is measured within 1-10 seconds from application of the sample. Based on this reading, the hematocrit volume fraction is calculated.

The plasma ferritin concentration is read after an incubation period of about 5 minutes, and the ferritin concentration presented with consideration of the previously calculated Hct for the sample. Assuming a normal distribution of the Hct for men and women (within the intervals indicated by Henny H. Billett, 1990, ibid) the use of the measured Hct instead of an average for each gender, or an average for all patients, resulted in an improved accuracy for a majority of patients.

Example 3. Plasma Calprotectin

Calprotectin in plasma and blood is a useful biomarker of inflammation and infection, and a POC test for determining calprotectin in a whole blood sample would be a significant improvement. Here it however becomes extremely important to take the correct Hct into account, as variations in Hct will influence the amount of plasma available for the assay. In a theoretical example, the inventors postulate that a calprotectin value in plasma of 1.5 mg/l can be significantly under- as well as overestimated in cases of high or low Hct values, values still within the normal ranges for adult men and women.

As shown in the table below, a true value of 1.5 mg/ml calprotectin in plasma will be displayed as 1.30 mg/l for male patients having a high Hct while still in the normal Hct range. Conversely, the value will be significantly overestimated for patients having low Hct, 1.70 mg/l for male patients, and 1.66 mg/l for female patients having a low Hct. Such errors may lead to an incorrect diagnosis.

For patients with Hct values outside the normal range, the error will be even more significant.

TABLE 1

| Impact of Hct level on plasma calprotectin determination | | |
|---|---|---|
| | Males | Females |
| Hct range (mean) | 40-54% (47%) | 36-48% (42%) |
| Example given: 1.50 mg/l plasma calprotectin | | |
| Hct low | 1.70 mg/l | 1.66 mg/l |
| Hct mean | 1.50 mg/l | 1.50 mg/l |
| Hct high | 1.30 mg/l | 1.34 mg/l |

The above was later confirmed in practical experiments, using a lateral flow assay platform, equipped with a glass fiber filter for separating plasma, and for allowing the instantaneous measurement of Hct.

Calprotectin is one example of an analyte for which a moderate dilution, e.g. a factor 10-50 may be suitable. Example 13 shows how the degree of dilution and colour of illumination light (IR/red/green/blue) affects the Hb determination ability from image-based reflectance measurements.

Example 4. Cystatin C

Cystatin C is a small protein with a basic isoelectric point that has emerged as an alternative marker for kidney function. The justification for the use of cystatin C as a marker for renal function follows the same basic logic as that for creatinine. Since cystatin C is not secreted and does not return to the blood stream but rather is reabsorbed by tubular epithelial cells and subsequently degraded, it avoids some of the non-renal effectors such as muscle mass, age or gender that complicate the use of other endogenous markers.

It has been shown that increased levels of cystatin C are associated with a higher risk of death from all causes, and the highest quintile of cystatin C ($\geq$1.29 mg/l) is associated with a significantly elevated risk of death from cardiovascular causes, myocardial infarction, and stroke after multivariate adjustment. It was concluded that cystatin C is a stronger predictor of the risk of death and cardiovascular events in elderly persons than is creatinine (Shiplak et al., 2005).

The inventors postulate that a Cystatin C value in plasma can be significantly under- as well as overestimated in cases of high or low Hct values, values still within the normal ranges for adult men and women. As shown in Table 2 below, a true value of 1.03 mg/ml in plasma will be displayed as 0.89 mg/l for male patients, and 0.92 mg/l for female patients having a high Hct while still in the normal Hct range. Conversely, the value will be significantly overestimated for patients having low Hct. Such errors may lead to an incorrect diagnosis. Unidentified outliers, i.e. patients with a very low Hct or very high Hct will be subject to very inaccurate measurement of plasma cystatin C values, and an inaccurate estimation of glomerular filtration rates.

TABLE 2

| Impact of Hct level on cystatin C determination | | |
|---|---|---|
| | Males | Females |
| Hct range (mean) | 40-54% (47%) | 36-48% (42%) |
| Cystatin C plasma value | 1.00 mg/l | 1.00 mg/l |
| Hct low | 1.13 mg/l | 1.10 mg/l |
| Hct mean | 1.00 mg/l | 1.00 mg/l |
| Hct high | 0.87 mg/l | 0.90 mg/l |

Example 5. Ferritin

It is generally known that the ferritin concentration in plasma reflects the size of the iron reserve in the body. Ferritin has been studied in large-scale surveys of the iron status of populations. It has also been found useful in the assessment of clinical disorders of iron metabolism. A low plasma ferritin level has a high predictive value for the diagnosis of uncomplicated iron deficiency anaemia. The normal range for blood ferritin is 20 to 500 nanograms per millilitre (for adult men) and 20 to 200 nanograms per millilitre (for adult women). Recently, the ferritin-to-hemoglobin ratio has been suggested as a useful tool to predict survival in patients with advanced non-small-cell lung cancer (NSCLC). The ferritin-to-hemoglobin ratio, a potential parameter of tumour progression, was a significant prognostic factor for overall survival, with a direct correlation to survival time in patients with advanced NSCLC (Sookyung Lee et al., 2019).

The inventors postulate that the measurement of ferritin, as well as all biomarkers in plasma, is highly dependent on the hematocrit, and that the concentration of ferritin can be significantly under- as well as overestimated in cases of high or low Hct values, values still within the normal ranges for adult men and women. This becomes more important as new diagnostic applications of the ferritin concentration are presented. The influence of variations in Hct on ferritin measurements is illustrated in the table below.

TABLE 3

| Impact of Hct level on plasma (liver) ferritin determination | | |
|---|---|---|
| | Males | Females |
| Hct | 40-54% | 36-48% |
| Ferritin range (ug/l) | 20-300 | 15-200 |
| Low Hct | 23-339.62 | 16.55-220.69 |
| High Hct | 17.36-260.38 | 13.45-179.31 |
| Example given: 25 µg/l plasma ferritin | | |
| Low Hct | 28.30 µg/l | 27.59 µg/l |
| High Hct | 21.70 µg/l | 22.41 µg/l |

The inventors postulate that the plasma ferritin value will be overestimated in patients having a low Hct, and underestimated in patients having high Hct, which can result in low ferritin values being overlooked.

The present inventors tested their hypothesis experimentally. Lateral flow test strips were assembled using a 17×5 mm sample pad VF2 (GE Healthcare), a 8×5 mm conjugate release pad (8964 glass fibre membrane, Ahlstrom-Munksjö AB) a 25×5 mm nitro cellulose membrane (CN180, 25 mm, Sartorius) and a 17×5 mm absorbent pad (17 mm Grade 222, Ahlstrom-Munksjö). The conjugate release pad was pretreated with 80 nm gold conjugate (Innovacoat gold 80 nm, Expedeon Ltd.). Prior to dispensing the gold particles to the conjugate pad, the gold nanoparticles were conjugated to polyclonal rabbit anti human ferritin (product code BP230-3, BBI solutions) according to instructions from manufacturer and finally diluted to OD 20 in a buffer comprising 2 mM borate, 10% sucrose, 1 mL/L sodium azide (10% solution), pH 9.5. The conjugate was dispensed at 5 μL/cm. A test line (T line) was printed on the nitrocellulose using the same polyclonal rabbit anti human ferritin at a concentration of 0.7 mg/ml, 5 μl/cm and a control line (C line) using goat anti rabbit IgG (product code SAB3700883, Sigma) at a concentration of 1 mg/ml, 5 μl/cm. The test strips were assembled in a housing (Inplastor AB).

A blood sample was obtained from a healthy volunteer. From this sample, five different blood aliquots with different hematocrit levels (Hct) were prepared by mixing the red blood cell (RBC) fraction and the plasma fraction in different proportions. The plasma ferritin concentration was the same in all samples. The Hct level of each sample was assigned by centrifugation (Haematokrit 200 centrifuge, Andreas Hettich GmbH & Co. KG, Tuttlingen, Germany) and the Hb levels were assigned using HemoCue 201+ (HemoCue AB, Ängelholm). The Hct levels ranged from ~38% to ~52%. A sample of 12.5 μl whole blood was mixed with 87.5 μl of a buffer that do not induce lysis of RBC (0.1 M Tris-HCl, 0.05 M NaCl, 1% BSA, 1% Tween 20, pH 7.4). 75 μl of the blood buffer mixture was pipetted onto the VF2 sample pad, and the Hct read after the sample had been absorbed into the substrate.

After 15 min, the intensity of the T (test) and C (control) line was measured using a Cube reader (opTricon GmbH, Berlin, Germany). 10 replicates were performed per Hct level, giving a total of 50 measurements. The intensity of the T and C lines, respectively, were quantified using the software of opTricon's Cube reader (mean function). The T/C ratio was quantified for each of the 50 measurements. The T/C ratio correlates with the ferritin level of the sample. The precision in the T/C ratio, without considering variations in the Hct levels, was calculated to a CV of 12.5%. By accounting for the assigned Hct level the precision improved to a CV of 10.6%; indicating that quantifying and correcting for differences in Hct levels improves the overall precision of the assay. This shows that a proper Hct determination and correction adds value in whole blood lateral flow assays where a plasma protein is to be accurately quantified.

Example 6. PCT—Plasma Procalcitonin

In another theoretical example, the inventors postulate that a plasma procalcitonin value of 0.15 μg/l can be significantly under- as well as overestimated in cases of high or low Hct values, values still within the normal ranges for adult men and women. As shown in the table below, a true value of 0.15 μg/l in plasma will be displayed as 0.13 μg/l for patients having a high Hct while still in the normal Hct range. Conversely, the value will be significantly overestimated (0.17 μg/l) for patients having low Hct. Such errors may lead to an incorrect diagnosis.

For patients with Hct values outside the normal range, the error will be even more significant.

TABLE 4

| Impact of Hct level on plasma procalcitonin determination | | |
|---|---|---|
| | Males | Females |
| Hct range (mean) | 40-54% (47%) | 36-48% (42%) |
| Example given: 150 ng/L plasma procalcitonin | | |
| Low Hct | 170 ng/L | 166 ng/L |
| Mean Hct | 150 ng/L | 150 ng/L |
| High Hct | 130 ng/L | 134 ng/L |

General considerations (information from Mayo Clinic Laboratories): In children older than 72 hours and in adults, levels below 0.15 ng/mL make a diagnosis of significant bacterial infection unlikely. Procalcitonin (ProCT) between 0.15 and 2.0 ng/mL does not exclude an infection, because localized infections (without systemic signs) may be associated with such low levels. Levels above 2.0 ng/mL are highly suggestive of systemic bacterial infection/sepsis or severe localized bacterial infection, such as severe pneumonia, meningitis, or peritonitis. They can also occur after severe non-infectious inflammatory stimuli such as major burns, severe trauma, acute multiorgan failure, or major abdominal or cardiothoracic surgery. In cases of non-infectious elevations, ProCT levels should begin to fall after 24 to 48 hours.

Autoimmune diseases, chronic inflammatory processes, viral infections, and mild localized bacterial infections rarely lead to elevations of ProCT of more than 0.5 ng/mL.

Example 7. C-Reactive Protein—CRP

In this theoretical example, the inventors postulate that a CRP value in plasma of 5 mg/l can be significantly under- as well as overestimated in cases of high or low Hct values, values still within the normal ranges for adult men and women. As shown in the table below, a true value of 5 mg/ml in plasma will be displayed as 4.34 mg/l for male patients having a high Hct while still in the normal Hct range. Conversely, the value will be significantly overestimated for patients having low Hct. Such errors may lead to an incorrect diagnosis.

For patients with Hct values outside the normal range, the error will be even more significant. This may have significant consequences when conducting a high-sensitive CRP test (hs-CRP). An hs-CRP test is performed to evaluate a patient's risk of heart disease. The current risk levels used are:

An hs-CRP level of less than 2.0 milligram per liter (mg/L) indicates a lower risk, while an hs-CRP level greater than 2.0 mg/L indicates an increased risk.

The below table indicates that there is a risk that the hs-CRP values will be underestimated in patients having a high Hct. This in turn could lead to that patients running a risk for contracting heart diseases would not be identified. For patients with even higher Hct, so called outliers, the error will be even greater.

TABLE 5

| Impact of Hct level on C-reactive protein determination | | |
|---|---|---|
| | Males | Females |
| Hct | 40-54% | 36-48% |

TABLE 5-continued

| Example given: 5 mg/l CRP | | |
|---|---|---|
| Low Hct | 5.66 mg/l | 5.52 mg/l |
| High Hct | 4.34 mg/l | 4.48 mg/l |

CRP is one example of an analyte where a significant dilution of the whole blood sample may be suitable, for example diluting at a dilution factor above 50, for example a factor of about 100 to about 2500. It is shown in Example 13 how the degree of dilution and colour of illumination light (IR/red/green/blue) affects the Hb determination ability from image-based reflectance measurements.

Example 8. Evaluation of Different Substrates

In this experiment, 12 different substrates, commercially available blood filters, were evaluated to determine their suitability for the Hct measurement. For each substrate type, 6 lateral flow strips were assembled from the following components 17×5 mm sample pad (the substrate to be evaluated), a 7×5 mm conjugate release pad GFCP203000 (Merck Millipore), a 60×5 mm nitrocellulose membrane Hi-Flow Plus 90 (Merck Millipore) and a 17×5 mm absorbent pad CFSP001700 (Merck Millipore). In total, 72 lateral flow strips were made.

Each substrate was evaluated with a high and a low Hct sample prepared in the laboratory. The high Hct sample had a Hct of 54% as determined using centrifugation (Haematokrit 200 centrifuge, Andreas Hettich GmbH & Co. KG, Tuttlingen, Germany) and the a Hb level of 180 g/l assigned with a HemoCue 201+(HemoCue AB, Ängelholm). The low Hct sample had a Hct of 30% and a Hb of 100 g/l, determined as above. Before application to the substrate, the samples were diluted by adding 175 μl isotonic chase buffer to 25 μl sample, and 100 μl of the diluted sample was added to the test (only 60 μl to the polysulfone-based Vivid GF, GR and GX membranes). In total 3 low Hct samples and 3 high Hct samples were run on each substrate type.

The different substrates before (blank) and after addition of sample were imaged using a Pixelink PL-D795MU-5MP monochrome camera (5 MP, 2/3 sensor) equipped with a VZM 100i video lens (Edmund Optics) and an 800 nm optical band pass filter (Thorlabs; FB800-10).

Figures 9A, 9B:
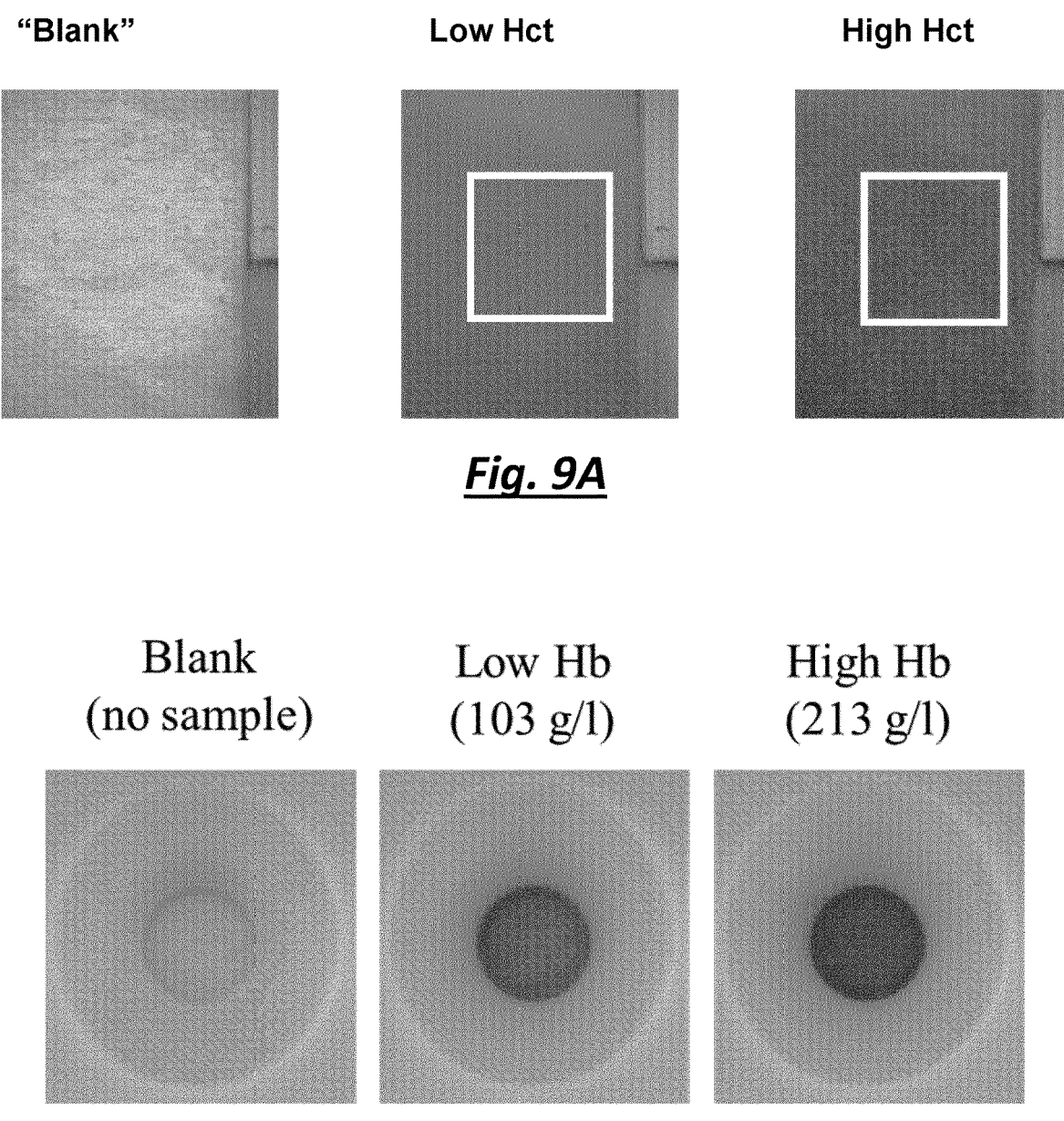
FIG. 9A consists of three photographs showing in order from left to right: the substrate (VF2, GE Healthcare) without added sample, a so called "blank" or zero measurement; the same substrate with a sample of "low Hct" added; and the same substrate with a sample of "high Hct". The white outline of a square indicates the ROI square (size 1000×1000 pixels) placed at the centre of the sample addition area. The substrate is illuminated with white light, and an optical filter applied before the camera.
FIG. 9B consists of three photographs showing in order from left to right: a sample well illuminated using a red LED without optical filters before the camera. The images (cropped) are from a ESEQuant Flex reader (Dialunox) and the samples were diluted by factor 10 before application to a Fusion 5 blood filter (Cytiva) placed in a DCN plastic housing.

The images were taken as 16-bit TIF (2048×2448 pixels) without gamma correction. Exposure time was set to 1500 ms. Two 50 W LED spotlights, having a colour temperature of about 2700 K, were used for illumination. For image analysis, performed in the R software, a ROI square was placed at the centre of the sample (size 1000×1000 pixels), and the mean pixel value within the square was calculated. This is illustrated in FIG. 9A showing in order from left to right: the substrate (VF2, GE Healthcare) without added sample, a so called "blank" or zero measurement; the same substrate with a sample of "low Hct" added; and the same substrate with a sample of "high Hct". The white outline of a square indicates the ROI square (size 1000×1000 pixels) placed at the centre of the sample addition area. FIG. 9B shows the corresponding images in a set-up where the diluted sample was applied to the sample pad and flow path enclosed in a plastic housing, where the sample addition well "frames" the sample.

Each blood image was corrected (division pixel-by-pixel) using an averaged image of three MF1 sample pads without any added sample (so called blanks). The mean pixel values were extracted from the central part of the images. The mean pixel intensity (at 800 nm) in the ROI square after background correction correlated with the assigned Hct values.

For each sample the mean pixel intensity, the "mean of mean" and standard deviation from mean, was calculated for the blank, and the high and low Hct samples respectively, and a CV (%) was determined for each substrate. The substrate samples evaluated are presented in Table 6, together with the results obtained, here shown as the difference between the values for the high and low Hct samples, as well as the average standard deviation. The first parameter indicates the distinguishing power of the substrate, and the second indicates the reproducibility o the results.

TABLE 6

| | Evaluation of different substrates | | |
|---|---|---|---|
| Substrate | Manufacturer | Difference (high:low) | Average STD |
| CytoSep ® | Ahlstrom-Munksjo, SE | 0.078 | 0.012 |
| FR1 035 | | 0.113 | 0.016 |
| FR1 060 | Advanced Microdevices Pvt. | 0.081 | 0.009 |
| FR2 070 | Ltd., India | 0.087 | 0.011 |
| Fusion 5 | Cytiva, USA | 0.073 | 0.006 |
| GFDVA | GE/Whatman | 0.085 | 0.004 |
| LF1 | GE/Whatman | 0.080 | 0.014 |
| MF1 | Cytiva, USA | 0.098 | 0.005 |
| VF2 | GE/Whatman | 0.090 | 0.015 |
| Vivid GF | Pall Co., USA | 0.056 | 0.014 |
| Vivid GR | | 0.036 | 0.007 |
| Vivid GX | | 0.040 | 0.004 |

The substrates GFDVA and MF1 were then subjected to an extended evaluation. 25 test strips (see above) were prepared for each substrate type. Five different blood samples were prepared: H1 (Hct 31.3% and Hb 101 g/l), H2 (Hct 37.5% and Hb 122 g/l), H3 (Hct 44.6% and Hb 145.5 g/l), H4 (Hct 51.7% and Hb 168 g/l), and H5 (Hct 58.0% and Hb 187.5 g/l). The samples spanned the physiologically relevant Hct levels (about 25-60%). A sufficient number of samples for five tests were prepared by mixing blood samples and buffer in a ratio of 12.5 μl blood to 87.5 μl isotonic chase buffer.

In the experiments, 75 μl of this mixture was added to the MF1 substrates, and 150 μl to the GFDVA substrates, as the GFDVA has a higher volume capacity. In total, 5 tests were run for each Hct level, and images taken and analysed as described for the other examples.

Example 9. Evaluating Substrate MF1 and Dilution Factor 4

Lateral flow test strips were assembled holding a 17×5 mm sample pad MF1 (GE Healthcare), a 7×5 mm conjugate release pad GFCP203000 (Merck Millipore), a 25×5 mm nitrocellulose membrane Hi-Flow Plus 90 (Merck Millipore) and a 17×5 mm absorbent pad CFSP001700 (Merck Millipore). A blood sample was obtained from a healthy volunteer. Five smaller aliquots with different hematocrit levels (Hct) were prepared by mixing the red blood cell (RBC) fraction and the plasma fraction in different ratios.

The Hct level of each sample was assigned by centrifugation (Haematokrit 200 centrifuge, Andreas Hettich GmbH & Co. KG, Tuttlingen, Germany) and the Hb levels were assigned with a HemoCue 201+(HemoCue AB, Ängelholm). The Hct levels ranged from ~25% to ~55%. For each measurement a sample of 25 μl whole blood was mixed with 75 µl of a buffer that do not induce lysis of RBCs (0.1 M Tris-HCl, 0.05 M NaCl, 1% BSA, 1% tween 20, pH 7.4). 75 µl of this blood buffer mixture was pipetted onto the MF1 sample pad and immediately imaged. For each Hct level five replicates were performed (i.e. n=5) as previously described. The glass fiber filter sample pads were imaged using a Pixelink PL-D795MU-5MP monochrome camera (5 MP, 2/3 sensor) equipped with a VZM 100i video lens (Edmund Optics) and an 800 nm optical band pass filter (Thorlabs; FB800-10).

Figure 10:
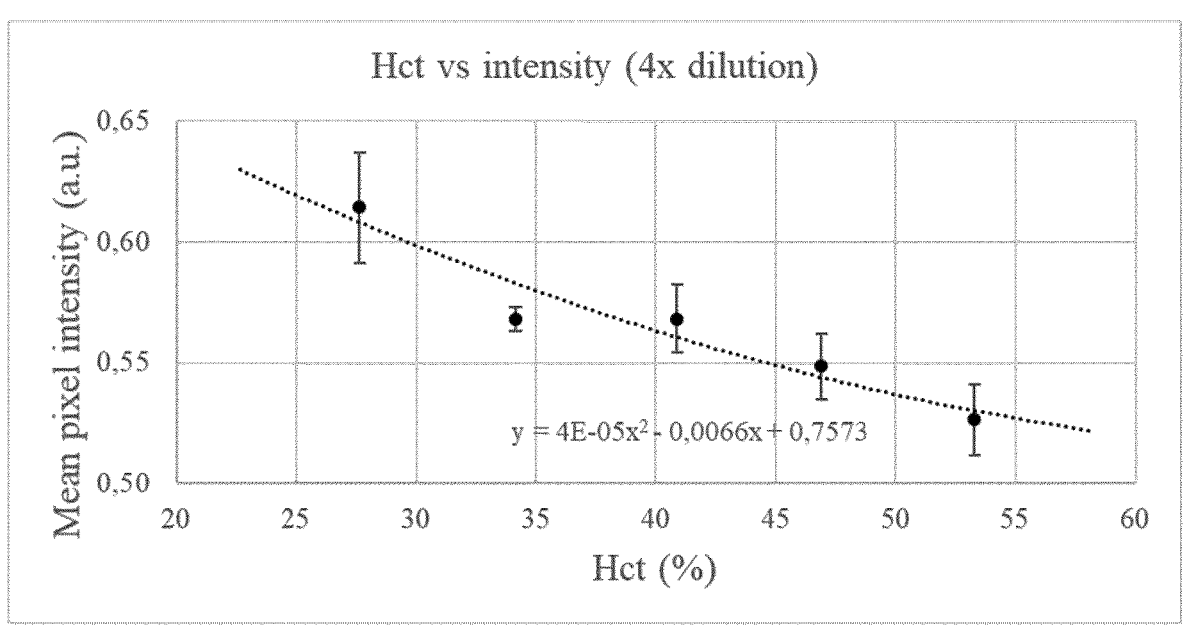
FIG. 10 is a graph showing the results from Example 9, here the mean pixel intensity plotted against Hct (%). In this experiment, the sample was diluted by a factor 4.

The images were taken as 16-bit TIF (2048×2448 pixels) without gamma correction. Exposure time was set to 1500 ms. Two 50 W LED spotlights, having a colour temperature of about 2700 K, were used for illumination. For image analysis, performed in the R software, a ROI square was placed at the centre of the sample image (size 1000×1000 pixels), and the mean pixel value within the square was calculated. Each blood image was corrected (division pixel-by-pixel) using an averaged image of three MF1 sample pads without any added sample (so called blanks). The mean pixel intensity (at 800 nm) in the ROI square after background correction correlated with the assigned Hct values. In this example, a 2nd degree polynomial was fitted to the measurements (See FIG. 10).

Figure 11:
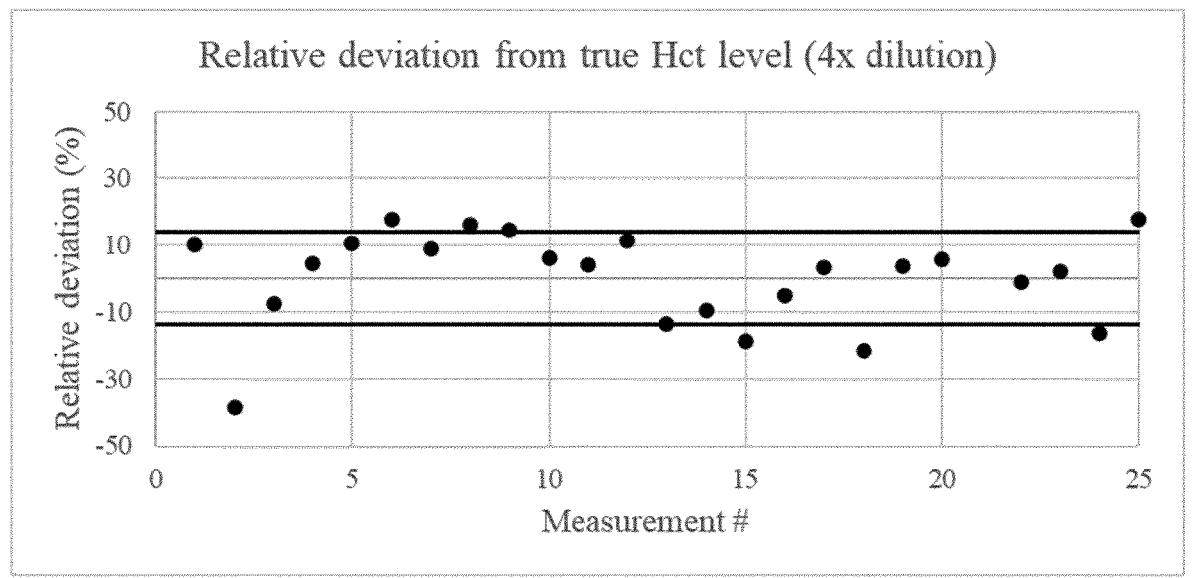
FIG. 11 is based on the results from Example 9 and shows the relative deviation from true Hct level obtained with dilution factor 4.

The inverse function of this 2nd degree polynomial served as a model to predict Hct level from the mean pixel intensity. Applying this prediction model to the obtained images, as described above, the present inventors calculated that predicted Hct levels deviated from assigned levels with a CV corresponding to 13.8% (See FIG. 11).

Example 10. Evaluating Substrate MF1 and Dilution Factor 8

Lateral flow test strips were assembled holding a 17×5 mm sample pad MF1 (GE Healthcare), a 7×5 mm conjugate release pad GFCP203000 (Merck Millipore), a 25×5 mm nitrocellulose membrane Hi-Flow Plus 90 (Merck Millipore) and a 17×5 mm absorbent pad CFSP001700 (Merck Millipore). A blood sample was obtained from a healthy volunteer. Five smaller aliquots with different hematocrit levels (Hct) were prepared by mixing the red blood cell (RBC) fraction and the plasma fraction in different ratios.

The Hct level of each sample was assigned by centrifugation (Haematokrit 200 centrifuge, Andreas Hettich GmbH & Co. KG, Tuttlingen, Germany) and the Hb levels were assigned with a HemoCue 201+(HemoCue AB, Ängelholm). The Hct levels ranged from ~30% to ~60%. For each measurement a sample of 12.5 µl whole blood was mixed with 87.5 µl of a buffer that do not induce lysis of RBCs (0.1 M Tris-HCl, 0.05 M NaCl, 1% BSA, 1% tween 20, pH 7.4). 75 µl of this blood buffer mixture was pipetted onto the MF1 sample pad and immediately imaged. For each Hct level five replicates were performed (i.e. n=5) as previously described. The glass fiber filter sample pads were imaged using a Pixelink PL-D795MU-5MP monochrome camera (5 MP, 2/3 sensor) equipped with a VZM 100i video lens (Edmund Optics) and an 800 nm optical band pass filter (Thorlabs; FB800-10).

Figure 12:
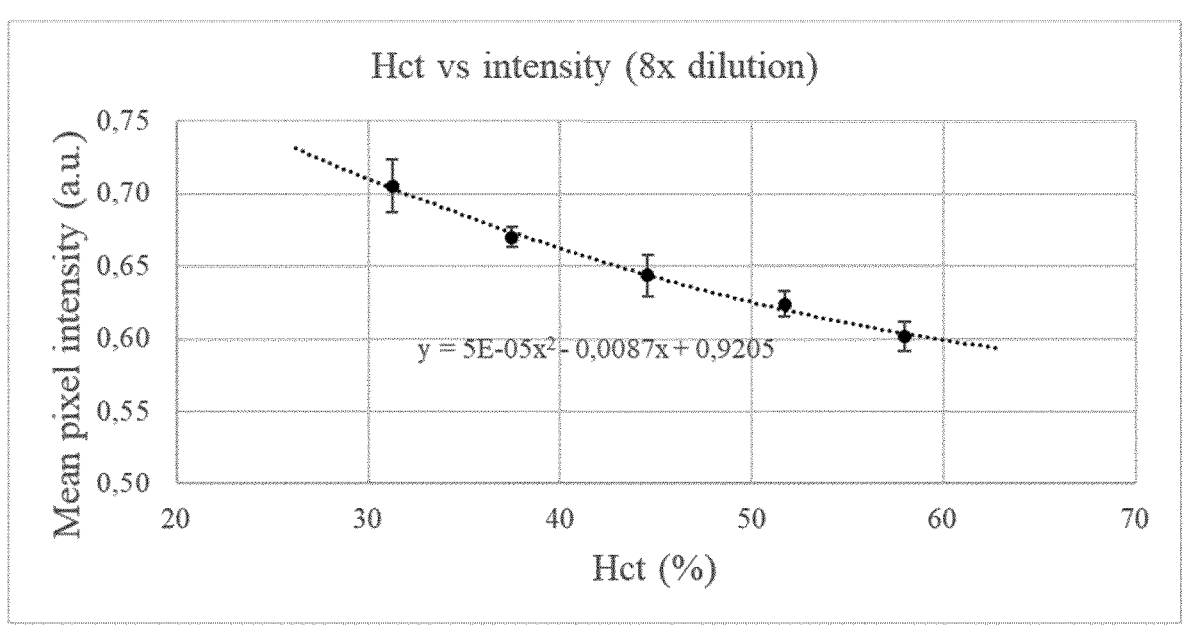
FIG. 12 is a graph showing the results from Example 10, here the mean pixel intensity plotted against Hct (%). In this experiment, the sample was diluted by a factor 8.

The images were taken as 16-bit TIF (2048×2448 pixels) without gamma correction. Exposure time was set to 1500 ms. Two 50 W LED spotlights, having a colour temperature of about 2700 K, were used for illumination. For image analysis, performed in the R software, a ROI square was placed at the centre of the sample image (size 1000×1000 pixels), and the mean pixel value within the square was calculated. Each blood image was corrected (division pixelby-pixel) using an averaged image of three MF1 sample pads without any added sample (so called blanks). The mean pixel intensity (at 800 nm) in the ROI square after background correction correlated with the assigned Hct values. In this example, a 2nd degree polynomial was fitted to the measurements (See FIG. 12).

Figure 13:
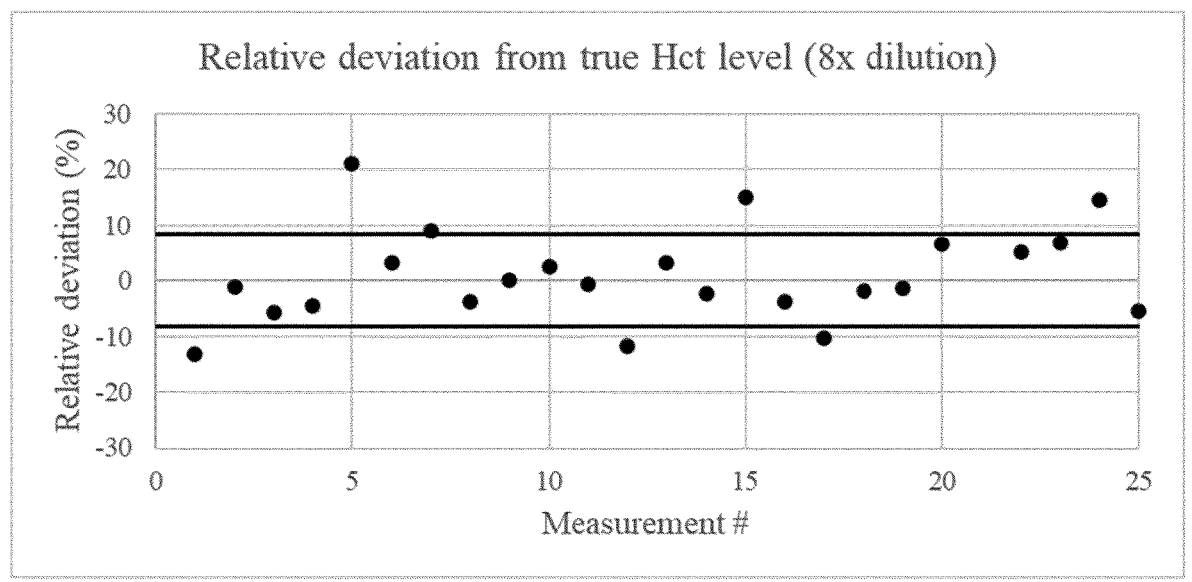
FIG. 13 is based on the results from Example 10 and shows the relative deviation from true Hct level obtained with dilution of the sample by a factor 8.

The inverse function of this 2nd degree polynomial served as a model to predict Hct level from the mean pixel intensity. Applying this prediction model to the obtained images, as described above, the present inventors calculated that predicted Hct levels deviated from assigned levels with a CV corresponding to 8.3% (See FIG. 13). Additionally, measurement no. 5 seems to be an outlier, possibly accountable to technical problems with the camera. If measurement no. 5 is disregarded, the CV improves to 7.4%.

Example 11. Time-Lapse Measurements with Substrate MF1 and Dilution Factor 4

Lateral flow test strips were assembled holding a 17×5 mm sample pad MF1 (GE Healthcare), a 7×5 mm conjugate release pad GFCP203000 (Merck Millipore), a 25×5 mm nitrocellulose membrane Hi-Flow Plus 90 (Merck Millipore) and a 17×5 mm absorbent pad CFSP001700 (Merck Millipore). A blood sample was obtained from a healthy volunteer. Aliquots with five different hematocrit levels (Hct) were prepared by mixing the red blood cell (RBC) fraction and the plasma fraction in different ratios.

The Hct of each sample was assigned by centrifugation (Haematokrit 200 centrifuge, Andreas Hettich GmbH & Co. KG, Tuttlingen, Germany) and the Hb levels were assigned using HemoCue 201+(HemoCue AB, Ängelholm). One of the prepared samples was used for a time-lapse study of the sample image. A sample was prepared by mixing 25 µl whole blood with 75 µl of a buffer that do not induce lysis of RBCs (0.1 M Tris-HCl, 0.05 M NaCl, 1% BSA, 1% tween 20, pH 7.4). 75 µl of the blood buffer mixture was pipetted onto the MF1 sample pad.

The sample was imaged using a Pixelink PL-D795MU-5MP monochrome camera (5 MP, 2/3 sensor) equipped with a VZM 100i video lens (Edmund Optics) and an 800 nm optical band pass filter (Thorlabs; FB800-10). The images were taken as 16-bit TIF (2048×2448 pixels) without gamma correction. Exposure time was set to 1500 ms. Two 50 W LED spotlights, having a colour temperature of about 2700 K, were used for illumination. Images were taken at t=0, 3, 5, 7, 10, 13, 15, 18, 20, 23, 25, 28 and 30 min, respectively. For image analysis, performed in the R software, a ROI square was placed at the centre of the sample image (size 1000×1000 pixels), and the mean pixel value within the square was calculated. Each blood image was corrected (division pixel-by-pixel) using an averaged image of three MF1 sample pads without any added sample (so called blanks). In this example, a prediction model linking mean pixel intensity to Hct level as described in relation to FIGS. 10 and 12, was used to predict the corresponding Hct level of the blood sample.

It can be clearly seen that the predicted Hct level drops over time, as the sample is aged, which is shown in FIG. 14. There is a slight decrease in the assigned hematocrit level over the first 10 minutes and the predicted value decreases with 3.2%. Between 10 and 15 minutes the decrease is faster and after 15 minutes the predicted value drops very fast. The value at 15 minutes is 7.2% lower than the value at t=0 and after 30 minutes the drop corresponds to 57.6%. The predictive power of the Hct prediction model, as described in relation to FIGS. 11 and 13, remains for around 10 min after the blood buffer mixture has been applied to the sample pad (MF1). After 10 minutes the sample starts drying and the appearance of the sample on the sample pad changes (see FIG. 14), and the model seems to predict lower and lower Hct levels.

Example 12. Mixing of Conjugates in Buffer (No Conjugate Pad)

Lateral flow test strips were assembled using a 24×5 mm sample pad MF1 (GE Healthcare), a 25×5 mm nitro cellulose membrane (CN180, 25 mm, Sartorius) and a 17×5 mm absorbent pad (17 mm Grade 222, Ahlstrom-Munksjo). A test line (T line) was printed on the nitrocellulose (product code BP230-3, BBI solutions) using polyclonal rabbit anti human ferritin at a concentration of 0.7 mg/ml, 5 µl/cm and a control line (C line) using goat anti rabbit IgG (product code SAB3700883, Sigma) at a concentration of 1 mg/ml, 5 µl/cm. The test strips were as shown schematically in FIGS. 4 and 6.

The test strips were assembled in a housing (Inplastor AB, Sweden) similar but not identical to the housing shown in FIG. 8. Gold nanoparticles (Innovacoat gold 80 nm, Expedeon Ltd) were conjugated to polyclonal rabbit anti human ferritin (product code BP230-3, BBI solutions) according to instructions from manufacturer. The conjugate was diluted to OD 0.6 in a sample buffer comprising 0.1 M Tris-HCl, 0.05 M NaCl, 1% BSA, 1% Tween 20, pH 7.4.

A blood sample was obtained from a healthy volunteer. Five different blood samples with different hematocrit levels (Hct) were prepared by mixing the red blood cell (RBC) fraction and the plasma fraction in different ratios. The plasma ferritin concentration was the same in all samples. The Hct level of each sample was assigned by centrifugation (Haematokrit 200 centrifuge, Andreas Hettich GmbH & Co. KG, Tuttlingen, Germany) and the Hb levels were assigned using HemoCue 201+(HemoCue AB, Ängelholm). The Hct levels ranged from −38% to ~52%.

A sample of 20 µl whole blood was mixed with 140 µl of a sample buffer that do not induce lysis of RBC (0.1 M Tris-HCl, 0.05 M NaCl, 1% BSA, 1% Tween 20, pH 7.4, gold conjugates at OD 0.6). 100 µl of the blood sample buffer mixture was pipetted onto the MF1 sample pad. After 15 min, the intensity of the T and C line was measured using the Cube reader (opTricon GmbH, Germany). 10 replicates were performed per Hct level, giving a total of 50 measurements. The intensity of the T and C lines, respectively, were quantified using the software of opTricon's Cube reader (mean function). The T/C ratio was quantified for each of the 50 measurements. The T/C ratio correlates with the ferritin level of the sample. The precision in the T/C ratio, without considering variations in the Hct levels, was calculated to a CV of 12.5%. By accounting for the assigned Hct level the precision improved to a CV of 10.6%; indicating that quantifying and correcting for differences in Hct levels improves the overall precision of the assay.

The inventors contemplate that further improvement of the precision will be achieved when method is refined, for example when the lateral flow assay strips are routinely manufactured, using automated equipment, and not manually as in the preparation of the current test strips.

The experiment however indicates that the conjugate pad is expendable, and that a highly simplified lateral flow assay strip can be used when the conjugates are included in the sample pad, or in the buffer. The experiment shows that a simplified method involving only one step of mixing the sample with a buffer to a pre-determined dilution factor allows the accurate determination of a biomarker in whole blood with simultaneous consideration of the Hct value of the sample.

By removing the conjugate pad, and instead mixing (i.e. conjugating) the sample in the buffer, the reaction kinetics of the conjugation reaction are improved. In a fibrous conjugate pad, the mixing and conjugation is dependent of how evenly and how efficiently the sample migrates through the conjugate pad, and also dependent on how evenly the reagents are deposited in the conjugate pad. Performing the conjugation reaction in a liquid media, the buffer, removes the possibility of such variations, and improves the repeatability of the assay.

In this example, gold nanoparticles conjugated to polyclonal rabbit anti human ferritin were used. In a preferred embodiment, monoclonal antibodies are used in order to avoid or minimize aggregation. Further, the gold nanoparticles can be replaced by other markers, for example blue latex nanoparticles. Preferably the markers are chosen so, that they do not interfere with the Hct measurement, i.e. chosen so that they exhibit minimal reflectance at the wavelength chosen for the Hct measurement.

Example 13. How the Degree of Dilution and Colour of Illumination Light (IR and Red/Green/Blue) Affects the Hb Determination Ability from Image-Based Reflectance Measurements; Using a Camera Based Lateral Flow Test Reader Lateral flow test strips were prepared by assembling 22×300 mm sample/conjugate pad Fusion 5 (Cat. No. 29009399, Whatman), 25×300 mm nitrocellulose membrane FP120HP (PN: 10547001, Whatman/GE) and a 17×300 mm absorbent pad CFSP001700 (Merck-Millipore) on a standard 60×300 mm backing card (PN: MIBA-040, DCN). The assembled 60×300 mm card was then cut into 5 mm wide strips using a CM5000 Guillotine Cutter (BioDot). The individual strips were then put in a standard housing for lateral flow tests (PN: MICA-200 BOTTOM/TOP, DCN). No antibodies were dispensed on the nitrocellulose membrane for these image-based reflectance measurements.

A venipuncture blood sample was collected from a healthy volunteer in one vacutainer tube (lithium-heparin, BD). Two different blood samples with vastly different hemoglobin (Hb) levels were prepared by mixing the red blood cell (RBC) fraction and the plasma fraction in predetermined ratios. The Hb level of these two samples were assigned using HemoCue 201+(HemoCue AB, Ängelholm) to 105.5 g/L ("low Hb") and 206.5 g/L ("high Hb"), respectively. Duplicates were averaged.

The two blood samples were diluted a factor 2.5, 10, 25, 100, 250, 1000 and 2500 in a buffer that does not induce lysis of the RBCs. The buffer used was a Tris buffer in saline, pH 7.5 with 0.5% tween and 0.5% non-fat dried milk. 75 µl of the diluted blood sample was dispensed into the sample application well of the test device (i.e. the housed test strip). After the diluted blood sample was fully absorbed into the sample/conjugate pad (Fusion 5), the sample application well of the test device was imaged with IR LED illumination, then by red LED illumination, then by green LED illumination and finally by blue LED illumination of an ESEQuant Flex reader (Dialunox). The IR LED illumination did not come as a default option but was separately customized. The resulting image, for each colour, consisted of an average of 10 images. For each dilution factor the imaging procedure for the low Hb and high Hb sample was repeated 5 times; making up a total of 70 images (per illumination colour) for this experiment series [2 Hb levels, 7 dilution factors, 5 repeats]. Note that 2.5× dilution for the blue LED and 2500× dilution for the IR LED were omitted on purpose due to lack of contrast between the low and high Hb samples.

The image analysis was performed in R (version 4.0.3) through the integrated development environment (IDE) RStudio (version 1.3.1093). From the images the pixels comprising the Fusion 5 filter (seen through the circular sample application well, cfr. FIG. 9B), having absorbed the diluted blood sample, were isolated using the "threshold" function. Their mean pixel value of the isolated area was calculated, which directly relates to the total amount of light reflected from the Fusion 5 filter. FIG. 16 illustrates how this mean pixel intensity depends on the degree of dilution (dilution factor) and illumination colour (IR/red/green/blue); and both low Hb and high Hb samples are included.

To estimate how well the Hb concentration of a blood sample can be predicted from individual images the inventors defined a contrast factor. This contrast factor was calculated for each illumination colour (IR, red, green, blue) and each dilution factor (2.5, 10, 25, 100, 250, 1000, 2500). The calculation of this contrast factor for a fixed dilution factor and illumination colour considers the 5 images of the diluted "low Hb" sample and the 5 images of the diluted "high Hb" sample. The average "mean pixel intensity" (AMPI) as well as the standard deviation of the "mean pixel intensity" (SDMPI) is calculated for each Hb level. Then, the contrast factor is defined as:

$$\text{Contrast} = [\text{AMPI}_{lowHb} - \text{AMPI}_{highHb}]/[\text{mean}(\text{SDMPI}_{lowHb};\text{SDMPI}_{highHb})]$$

Expressed in words, the contrast factor is defined as the difference in reflectance between the low Hb and the high Hb samples (with a certain dilution) put in relation to the variability in the reflectance measurements.

The calculated contrast factor for different illumination colours and dilution factors is presented in FIG. 17. The results clearly show that red LED illumination provides better possibilities for Hb concentration determination for dilution factors between approximately 2.5-50× dilution, whereas green or blue LED illumination is more suitable for 50×-2500× dilution.

The data presented in FIG. 17, were converted to estimated precision (CV %) in a Hb prediction model, based on the standard deviation for the measurements at low and high Hb and the assumption of a linear correlation between Hb and mean pixel intensity. The estimated precision for different dilution factors at different wavelengths is presented in FIG. 18.

Example 14. Establishing and Comparing Hb Predictability of Image-Based Reflectance Measurements Using Red and Green LED Illumination at Two Different Dilution Factors (10× and 100×)

Lateral flow test strips were prepared as described in Example 1. No antibodies were dispensed on the nitrocellulose membrane for these image-based reflectance measurements.

A venipuncture blood sample was collected from a healthy volunteer in one vacutainer tube (lithium-heparin, BD). Five different blood samples with hemoglobin (Hb) concentrations, spanning the better part of the physiologically relevant range, were prepared by mixing the red blood cells (RBC) fraction and the plasma fraction in pre-determined ratios. The Hb concentrations of these five samples were assigned using HemoCue 201+(HemoCue AB, Ängelholm) to 103.5 g/L, 128.0 g/L, 158.5 g/L, 183.5 g/L, and 209.5 g/L. Duplicates were averaged.

The five blood samples were diluted by a factor 10× and 100× in a buffer that does not induce lysis of the RBCs. The buffer composition was the same as disclosed in Example 13.

75 µl of the diluted blood sample was dispensed into the sample application well of the test device (i.e. the housed test strip). After the diluted blood sample was fully absorbed into the sample/conjugate pad (Fusion 5), the sample application well of the test device was imaged with red LED illumination, then by the green LED illumination in an ESEQuant Flex reader (Dialunox). The resulting image, for each colour, consisted of an average of 10 images. For each dilution factor the imaging procedure for the 5 diluted blood samples was repeated 5 times, making up a total of 50 images (per illumination colour) for this experiment series [5 Hb levels, 2 dilution factors, 5 repeats].

The image analysis was performed in R (version 4.0.3) through the integrated development environment (IDE) RStudio (version 1.3.1093). From the images the pixels comprising the Fusion 5 filter (seen through the circular sample application opening), having absorbed the diluted blood sample, were isolated using the "threshold" function. The mean pixel value of the isolated area was calculated, which directly relates to the total amount of light reflected from the diluted blood sample absorbed by the Fusion 5 filter. FIG. 18 illustrates how this mean pixel intensity depends on the Hb concentration of the original blood sample. Illustrated are the results from a) red LED illumination with 10× dilution, and b) green LED illumination with 100× dilution. Analogous results were obtained for red LED illumination with 100× dilution, and green LED illumination with 10× dilution (plots not included).

FIG. 19 illustrates the results as mean pixel intensity of diluted blood samples for the two settings a) red LED illumination at 10× dilution, and b) green LED illumination at 100× dilution. Each Hb concentration was measured 5 times. The circular dots represent the mean and the error bars represent 1 std. To each data set a power function was fitted to be used as a model for predicting the Hb concentration directly from the mean pixel intensity.

Figure 20:
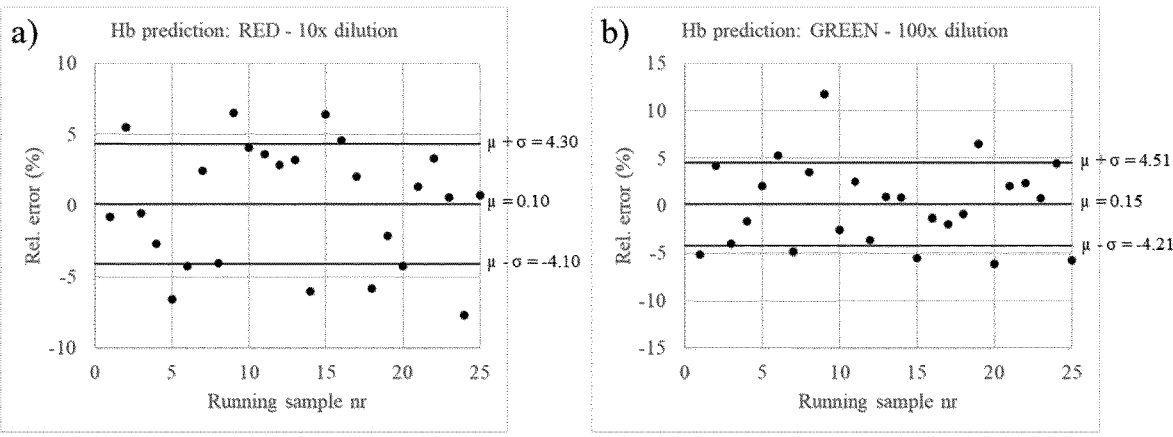
FIG. 20 shows two diagrams illustrating the performance of the two Hb concentration prediction models formulated in FIG. 19: a) the model for Red LED illumination and 10× dilution has a relative error of 0.10+/−4.20% and b) the model for Green LED illumination and 100× dilution has a relative error of 0.15+/−4.36%.

From the obtained dependencies between mean pixel intensity and Hb concentration power functions were fitted serving as models for predicting the Hb concentration from the mean pixel intensity; one model for each illumination colour and dilution factor. The performance of each model was evaluated with the same 25 data points it was formulated from. For red LED illumination the mean pixel intensity served as a better predictor at a dilution factor of 10× (compared to 100×). For green LED illumination the opposite was seen; the mean pixel intensity served as a better predictor at a dilution factor of 100× (compared to 10×). The performance of the best prediction model for each illumination colour are shown in FIG. 20. The performance, both in absolute and relative terms, of all four models are summarized in Table 7.

TABLE 7       TABLE 8

Performance of the four Hb concentration prediction models formulated from red and green illumination at 10x and 100x dilution, respectively. Red illumination yields smaller errors at 10x dilution, while green illumination yields smaller errors at 100x dilution.

| Illumination colour | Dilution factor | Abs. Error of model (1 std in g/l) | Abs. Bias of model (g/l) | Rel. Error of model (1 std in %) | Rel. Bias of model (%) |
|---|---|---|---|---|---|
| RED | 10 | 6.66 | 0.12 | 4.20 | 0.10 |
| GREEN | 10 | 15.44 | 0.83 | 9.48 | 0.56 |
| RED | 100 | 10.33 | 0.33 | 6.25 | 0.21 |
| GREEN | 100 | 6.65 | 0.22 | 4.36 | 0.15 |

From the results above it is evident that red LED illumination in reflectance-based Hb concentration determination performs significantly better than green LED illumination at lower dilution factors (here 10×). Likewise, green LED illumination performs significantly better than red LED illumination at higher dilution factors (here 100×).

Example 15. Theoretical Considerations on how Natural Hct Variations Directly Affect the Imprecision in Whole Blood Lateral Flow Assays When considering a strategy for Hct determination in a whole blood test for improved precision of the plasma biomarker determination it makes sense to consider natural variations in Hct levels in a healthy population. This in order to better understand how the overall precision of the test is affected by ignoring these variations. The theoretical considerations elaborated on herein are based on the following assumptions:

A. The Hct levels are normally distributed among the healthy population; separating men and women.

B. 95% of the population (i.e. +/−1.96 std) is included within the stated normal reference interval of Hct (Ref: Billett, 1990, ibid).

Women: 36-48%.

Men: 40-54%.

Figure 21:
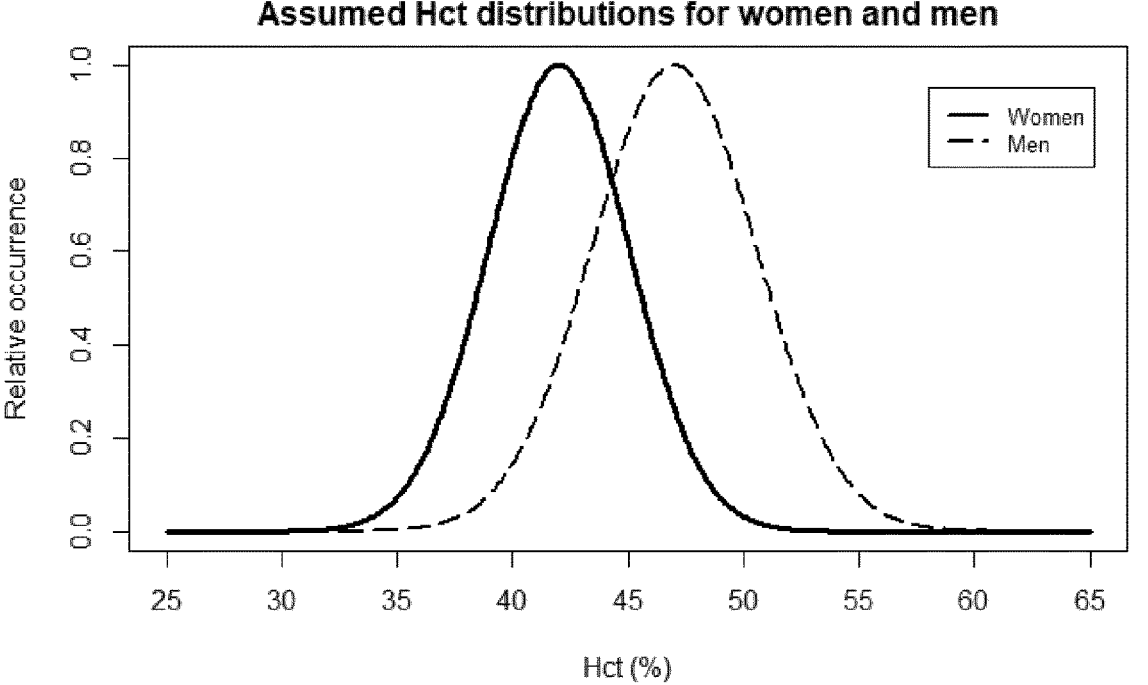
FIG. 21 is a graph illustrating the assumed distribution of Hct levels for healthy women and men.

FIG. 21 illustrates these two distributions. All calculations of average values consider an equal occurrence of women and men, as well as their respective Hct levels being solely based on the distributions as described above.

Variations in Hct levels directly affect the concentration determination of biomarkers in plasma as the correct plasma volume needs to be known for an accurate concentration determination. The calculations presented in Table 8 assumes that an equal amount (i.e. weight) of the biomarker always gives the same measured quantity, meaning that read-out is independent on the plasma volume in which the biomarker is present. A lower Hct level than accounted for gives an over-estimation of the concentration, and vice versa.

How the biomarker concentration determination is affected for individuals with different Hct levels when the accounting for either the overall mean Hct (44.5%) or gender specific mean (women: 42%, men: 47%)

| Gender: | Hct level: | Hct level (%): | Relative concentration when compensating for "mean Hct (all)": 44.5% | Relative concentration when compensating for "mean Hct (gender)": women: 42% men: 47% |
|---|---|---|---|---|
| Female | Very low | 30 | 126.1% | 120.7% |
| Male | Very low | 33 | 120.7% | 126.4% |
| Female | Low | 36 | 115.3% | 110.3% |
| Male | Low | 40 | 108.1% | 113.2% |
| Female | Mean | 42 | 104.5% | 100.0% |
| Male | Mean | 47 | 95.5% | 100.0% |
| Female | High | 48 | 93.7% | 89.7% |
| Male | High | 54 | 82.9% | 86.8% |
| Female | Very high | 54 | 82.9% | 79.3% |
| Male | Very high | 61 | 70.3% | 73.6% |

As described in Table 8 above, there are two basic ways of compensating for the Hct level to calculate the concentration of the biomarker in plasma. The first one being by using the average Hct level of all individuals (44.5%), and the second being by also considering gender (42% for women and 47% for men).

By considering the two strategies for guessing and putting them in relation to the assumed Hct distributions (FIG. 21) it is possible to calculate the precision (expressed as CV) of the Hct determination these both strategies result in.

Assuming all individuals has an Hct level of 44.5% yields a precision expressed of 9.5% (CV). Assuming an Hct level of 42% for all women and 47% for all men yields a precision of 7.4% (CV) for women and 7.8% (CV) for men. Hence, gender-based assumptions of Hct level gives a significantly better precision (CV=7.6%) compared to non-gender-based (CV=9.5%).

Figure 22:
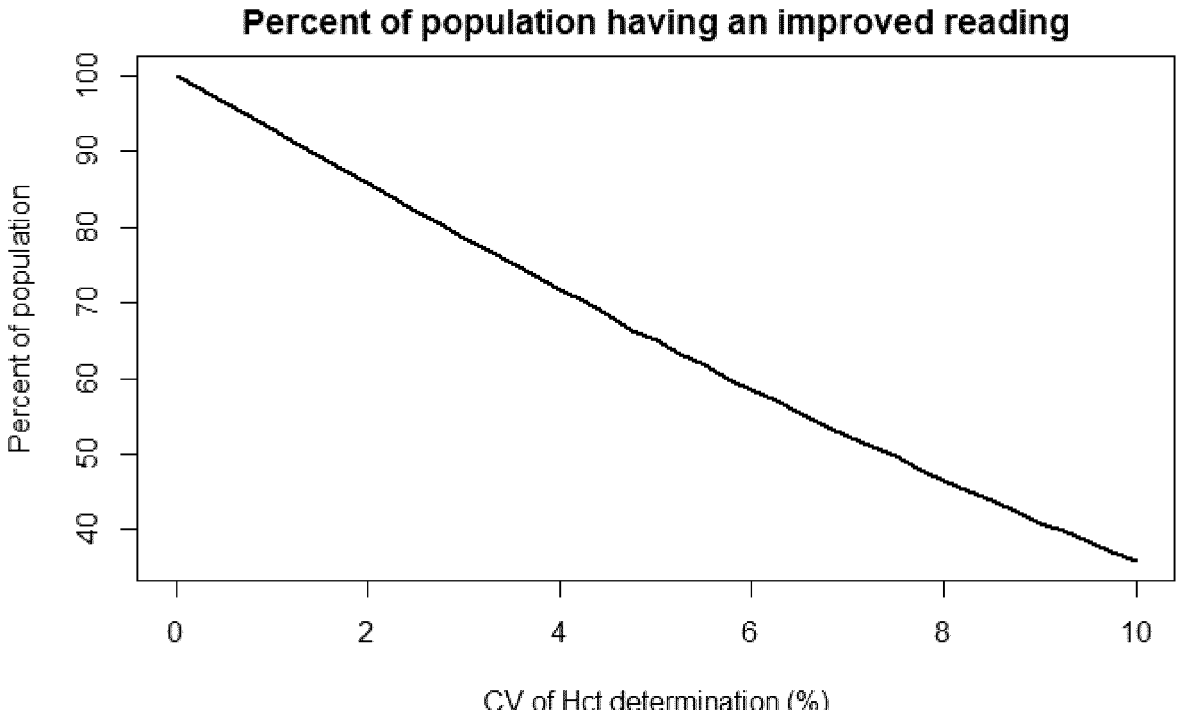
FIG. 22 is a graph illustrating the percent of population obtaining an improved reading using the inventive method.

By measuring the Hct level the situation can be improved further. FIG. 22 illustrates what fraction of the population that will have an improved Hct level determination as a function of the precision of the Hct level determination method. Once the precision of the determination method is smaller than ~7.5% the majority of the population will have an improved Hct level determination.

It is also worth noting that the part of the population with extreme Hct levels, either very low or very high, are more likely to benefit from an Hct level measurement rather than being subject to assumptions based on the average of a healthy population.

With a precision of the Hct determination corresponding to a CV of 5% women with Hct levels outside of the interval 40.6%-43.5% will on average have an improved reading. Men with Hct levels outside of the interval 45.5%-48.7% will on average have an improved reading. FIG. 22 illustrates what fraction of the total population that will have an improved Hct level determination as a function of the precision of said method.

From a benchmarking perspective the inventive method for Hct determination has a significantly better precision than a strategy of estimating the Hct level based on gender—which in itself gives credibility to the method. Furthermore, in relation to this comparison it is worthwhile noting that the reference interval for Hct levels the inventors have considered here are for healthy adults. In addition to specific disease states (e.g. erythrocytosis (Wouters et al., 2020) there are a multitude of factors that can offset the Hct levels on a population level.

In comparison to the reference intervals given above infants have somewhat broader Hct intervals, and may have higher Hct levels while young children, pregnant women (Stevens et al., 2013) as well as elderly (Tettamanti et al., 2010) often have lower Hct levels. Famine and malnutrition also reduce the Hct level on a group level. External factors such as living at higher altitude (>1500 m above sea level) and smoking on the other hand tend to elevate the Hct level.

Given all the factors affecting the Hct level mentioned above, an assay that relies on correcting the plasma marker concentration by assuming the average Hct level for a certain group of individuals will phase significant challenges.

To conclude, a more precise Hct determination suppresses the risk of both under- and over-estimating the sought biomarker. Given the physiological nature of the biomarker this will reduce the risk of taking a potentially adverse medical decision. For example, biomarkers that are upregulated in certain disease states (e.g. Cystatin C or CRP) should preferably not be under-estimated since this would potentially result in delayed treatment of the patient which might have severe consequences.

Furthermore, there are situations where biomarker level above or below a certain threshold (so called decision point) is used to deduce if an infection is of bacterial or viral origin (e.g. calprotectin), which guides the medical doctor in the treatment decision. An underestimation would result in delayed treatment of a bacterial infection which could potentially result in a worsening, leading to the severe condition of sepsis. An overestimation would on the other hand result in unnecessary use of antibiotics. In the context of blood donation an over-estimation of the amount of ferritin might indicate that the iron status of the donor is sufficient for donation.

Without further elaboration, it is believed that a person skilled in the art can, using the present description, including the examples, utilize the present invention to its fullest extent. Also, although the invention has been described herein with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

Non-Patent Literature

Attia et al., Determination of Human Hemoglobin Derivatives, Hemoglobin, 2015; 39(5): 371-374
Billett H. H., Chapter 151, Hemoglobin and Hematocrit, in Clinical Methods: The History, Physical and Laboratory Examinations, Walker H K, Hall W D, Hurst J W, eds., Boston: Butterworths; 1990. 3rd edition

40

Capiau, et al., A Novel, Non-destructive, Dried Blood Spot-Based Hematocrit Prediction Method Using Noncontact Diffuse Reflectance Spectroscopy, Analytical Chemistry. 2016, 88, 6538-6546
Jalal et al., Histogram analysis for smartphone-based rapid hematocrit determination, Biomed Opt Express. 2017 Jul. 1; 8(7): 3317-3328
Shiplak M. G. et al., Cystatin C and the Risk of Death and Cardiovascular Events among Elderly Persons, May 19, 2005, N Engl J Med 2005; 352:2049-2060
Sookyung Lee et al., Prognostic Value of Ferritin-to-Hemoglobin Ratio in Patients with Advanced Non-Small-Cell Lung Cancer, J Cancer 2019; 10(7):1717-1725. doi: 10.7150/jca.26853
Stevens G. A. et al., Global, regional, and national trends in haemoglobin concentration and prevalence of total and severe anaemia in children and pregnant and non-pregnant women for 1995-2011: a systematic analysis of population-representative data, The Lancet, VOLUME 1, ISSUE 1, E16-E25, Jul. 1, 2013
Tettamanti M et al., Prevalence, incidence, and types of mild anemia in the elderly: the "Health and Anemia" population-based study, Haematologica. 2010 November; 95(11):1849-56
Wouters H J C M et al., Erythrocytosis in the general population: clinical characteristics and association with clonal hematopoiesis, Blood Adv. 2020 Dec. 22; 4(24): 6353-6363
Yang et al., Simple Paper-Based test for Measuring Blood Hemoglobin Concentration in Resource-Limited Settings, Clinical Chemistry, (2013) 59:10, 1506-1513

PATENT LITERATURE

U.S. Pat. No. 8,730,460—Yan et al., Paper Based Spectrophotometric Detection of Blood Hemoglobin Concentration, published on Oct. 11, 2021
WO 2017/087834—Erickson et al., Multiplex Diagnostic Assay Cartridge for Detection of a Plurality of Target Molecules, published on May 26, 2017

The invention claimed is:

1. A lateral flow assay method for handling a sample of whole blood and determining a level of an analyte in a plasma fraction of said sample, comprising a step of determining a hematocrit value of said sample and applying said hematocrit value when determining the level of said analyte in said plasma fraction, characterized in that the method comprises the steps i) diluting said sample with a substantially non-hemolysing buffer to a pre-determined dilution factor, producing a diluted sample, ii) applying said diluted sample to a substrate of a lateral flow assay device, iii) taking an image of said substrate at a predetermined wavelength within 1-600 seconds from when the applied sample has been absorbed in said substrate, wherein the predetermined wavelength is based on the dilution factor used in step i), iv) analysing said image to determine a reflectance value from said image, v) correlating said value to values obtained for samples having known hematocrit values to obtain a value of hematocrit for said sample, vi) determining the level of said analyte down-stream in said lateral flow assay device, applying the dilution factor used in (i) and the hematocrit value of the sample obtained in (v) when determining the level of said analyte in the plasma.

2. The method according to claim 1, wherein the substrate is illuminated at a pre-determined wavelength when taking the image in step iii), and wherein said wavelength is selected based on the dilution factor used in step i).

3. The method according to claim 1, wherein the substrate is illuminated with white light and the image taken in step iii) is taken using an optical filter transmitting light of a pre-determined wavelength, and wherein said transmitted wavelength is selected based on the dilution factor used in step i).

4. The method according to claim 2, wherein the sample is diluted with an isotonic buffer to a dilution factor in the interval of 1-2500.

5. The method according to claim 2, wherein said image is taken while illuminating the substrate with applied sample with light having a wavelength in the interval of about 600 to about 950 nm when the dilution factor is 1 (no dilution) to 10.

6. The method according to claim 2, wherein said image is taken while illuminating the substrate with applied sample with light having a wavelength in the interval of about 575 nm to about 950 nm when the dilution factor is above 10 but below 50.

7. The method according to claim 2, wherein said image is taken while illuminating the substrate with applied sample with light having a wavelength in the interval of about 400 nm to about 575 nm when the dilution factor is 50 to 2500.

8. The method according to claim 3, wherein said image is taken while illuminating the substrate with applied sample with white light and using an optical filter transmitting light having a wavelength in the interval of about 600 nm to about 950 nm when the dilution factor is 1 (no dilution) to 10.

9. The method according to claim 3, wherein said image is taken while illuminating the substrate with applied sample with white light and using an optical filter transmitting light having a wavelength in the interval of about 575 nm to about 950 nm when the dilution factor is above 10 but below 50.

10. The method according to claim 3, wherein said image is taken while illuminating the substrate with applied sample with white light and using an optical filter transmitting light having a wavelength in the interval of about 400 nm to about 575 nm when the dilution factor is 50 to 2500.

11. The method according to claim 1, wherein the image is taken at a time chosen from within about 1 to about 600 seconds, about 1 to about 360 seconds, about 1 to about 180 seconds, and about 1 to about 90 seconds from when the sample has been absorbed in said substrate.

12. The method according to claim 1, wherein said substrate is a fibrous substrate capable of separating red blood cells and plasma.

13. The method according to claim 12, wherein said fibrous substrate is adapted to substantially avoid hemolysis of red blood cells in the sample.

14. The method according to claim 1, wherein the analyte is chosen from ferritin, transferrin, plasma calprotectin, C-reactive protein (CRP), cystatin C, plasma procalcitonin (PCT), NTproBNP, troponin T, troponin I, and anti-CCP antibodies.

15. A computer program product comprising software instructions stored in a memory, said software instructions executing, on a processor, the method according to claim 1.

* * * * *